(12) United States Patent
Alaimo et al.

(10) Patent No.: US 7,271,152 B2
(45) Date of Patent: *Sep. 18, 2007

(54) COMPOUNDS AND METHODS FOR THE MODULATION OF CD154

(75) Inventors: Lisa Alaimo, Los Altos, CA (US); Veronica Alves, Pleasant Hill, CA (US); Patrick Andre, San Mateo, CA (US); David Phillips, San Mateo, CA (US); Sri R. Prasad, Palo Alto, CA (US); Denisa D. Wagner, Dover, MA (US)

(73) Assignee: CBR Institute for Biomedical Research, Boston, MA (US)

( * ) Notice: Subject to any disclaimer, the term of this patent is extended or adjusted under 35 U.S.C. 154(b) by 386 days.

This patent is subject to a terminal disclaimer.

(21) Appl. No.: 10/476,237

(22) PCT Filed: May 3, 2002

(86) PCT No.: PCT/US02/13900

§ 371 (c)(1),
(2), (4) Date: Jul. 8, 2004

(87) PCT Pub. No.: WO02/089730

PCT Pub. Date: Nov. 14, 2002

(65) Prior Publication Data

US 2004/0248813 A1 Dec. 9, 2004

Related U.S. Application Data

(63) Continuation-in-part of application No. 10/002,585, filed on Nov. 30, 2001.

(60) Provisional application No. 60/289,049, filed on May 3, 2001.

(51) Int. Cl.
*A61K 38/04* (2006.01)

(52) U.S. Cl. .................................. 514/19; 514/575
(58) Field of Classification Search .................. None
See application file for complete search history.

(56) References Cited

U.S. PATENT DOCUMENTS

| 5,595,885 A * | 1/1997 | Stetler-Stevenson et al. .... 435/69.2 |
| 5,691,382 A | 11/1997 | Crimmin et al. |
| 6,861,504 B2 * | 3/2005 | Phillips et al. ............. 530/301 |

OTHER PUBLICATIONS

Federici et al., The Journal of Clinical Investigation, 2005, vol. 115, No. 12, pp. 3494-3505.*
Sommer et al., Neuroscience Letters, 1997, vol. 237, pp. 45-48.*
"Integrilin", *Millennium Pharmaceuticals, Inc.* Product description.
"Matrix Metalloproteinases (MMPs) Inhibitors of MMPs'.", *Calbiochem.* Product description, Cat. Nos. 324385, 364205 and 444274., unknown.
Ondetti, et al., "MMP Inhibitors and TAPI Quick Reference", *Peptide International, Inc.* Product description, unknown.

* cited by examiner

*Primary Examiner*—Cecilia J. Tsang
*Assistant Examiner*—Roy Teller
(74) *Attorney, Agent, or Firm*—Gosz & Partners LLP

(57) ABSTRACT

The present invention relates to compounds that are capable of modulating CD154 mobilization and that are useful for stabilizing the thrombotic process and reducing the activation of cells involved in an inflammatory response. The present invention also relates to methods useful for identifying such compounds. The present invention also relates to the treatment of platelets for transfusion with metalloproteinase inhibitors to treat or prevent inflammation. The present invention also includes compositions and methods to treat injury and disease related to such biological processes.

44 Claims, 9 Drawing Sheets

CD40L in arterial thrombogenesis
collagen-coated perfusion chamber (2)

| | WT | | | CD40L-/- | | |
|---|---|---|---|---|---|---|
| | 650 3' | 1600 3' | 3200 2'15" | 650 3' | 1600 3' | 3200 2'15" |
| Surface covered with platelets (%) | 39.8 ± 4.5 | 57 ± 1.9 | 57.8 ± 3.4 | 40.7 ± 3.1 | 55 ± 2.7 | 56.7 ± 3 |
| Mean thrombus height (μm) | 17 ± 3.5 | 32 ± 2 | 19.4 ± 1.7 | 18.5 ± 3 | 27.4 ± 1.2 | 10.7 ± 2.1* | n = 3 experiments: 1 mouse / chamber at 650 $s^{-1}$
2 mice pooled / chamber at 1600 $s^{-1}$
3 mice pooled / chamber at 3200 $s^{-1}$     * $P < 0.05$

Fig. 1

SEQUENCE LISTING

```
<160> NUMBER OF SEQ ID NOS: 2

<210> SEQ ID NO 1
<211> LENGTH: 35
<212> TYPE: DNA
<213> ORGANISM: Homo sapiens

<400> SEQUENCE: 1
cgaattcctc ttccatggaa aacagctttg aaatg                                35

<210> SEQ ID NO 2
<211> LENGTH: 29
<212> TYPE: DNA
<213> ORGANISM: Homo sapiens

<400> SEQUENCE: 2
gactcttcga agctaggatc ctagggtta                                       29
```

COMPOUNDS AND METHODS FOR THE MODULATION OF CD154

CROSS-REFERENCE TO RELATED APPLICATIONS

This application is a national stage filing under 35 U.S.C. 371 of International Application PCT/US02/13900, filed May 3, 2002, which claims priority from U.S. Application No. 60/289,049, filed May 3, 2001 and U.S. application Ser. No. 10/002,585, filed Nov. 30, 2001, the specifications of each of which are incorporated by reference herein. International Application PCT/US02/13900 was published under PCT Article 21(2) in English.

RELATED APPLICATIONS

This application is a continuation-in-part of U.S. application Ser. No. 10/002,585, filed Nov. 30, 2001 and claims the benefit of priority under 35 U.S.C. §119(e) to U.S. Provisional Application No. 60/289,049 filed on May 3, 2001, both of which are incorporated herein by reference in their entirety.

FIELD OF THE INVENTION

The present invention relates to compounds that are capable of specifically modulating CD154 mobilization and that are useful for stabilizing the thrombotic process and reducing the activation of cells involved in an inflammatory response. The present invention also relates to methods useful for identifying compounds suitable for modulating the release of CD154. The invention also relates to the treatment of platelets for transfusion with metalloproteinase inhibitors to treat or prevent inflammation and to enhance the viability of platelets, following transfusion. The present invention also includes compositions and methods to treat injury and disease related to such biological processes.

BACKGROUND OF THE INVENTION

Platelet aggregation, activation and adhesion to endothelial cells and extracellular matrix proteins are crucial events in the development of atherosclerosis and arterial cardiovascular diseases. Platelet activation is initiated by stimulation of intracellular signaling cascades, including the p42 mitogen-activated protein kinase (MAPK) and p38 MAPK pathways, followed by major changes in the platelet cytoskeleton and expression and activation of platelet surface receptors, such as P-selectin (CD62P) and CD154.

Mural and intraplaque arterial thrombi are composed primarily of platelet aggregates and are physically associated with developing lesions. Activated platelets present in a platelet-rich arterial thrombi directly bind to vascular endothelial cells, smooth muscle cells, and other cells within an atheroma, via CD154/CD40 interactions. This binding induces inflammatory reactions that have the potential of initiating or hastening the development of atherosclerotic lesions, as detected by the release of inflammatory cytokines and the surface expression on endothelial cells of adhesion receptors and tissue factor. This pathway is also important for T cell-induced monocyte and endothelial cell procoagulant activity. It is believed that human clinical trials are currently underway, designed to study whether the administration of soluble CD154 can enhance immune response in certain patients.

Platelets co-localize with leukocytes at sites of hemorrhage, within atherosclerotic and postangioplasty restenotic lesions, and in areas of ischemia-reperfusion injury. This interaction between platelets and leukocytes illustrates the biological links between hemostatic/thrombotic and inflammatory responses. It has been suggested that inflammation and thrombosis are more intertwined in the processes of vascular disease than was previously appreciated.

The vascular endothelium influences the three classically interacting components of hemostasis: blood vessels, platelets, and the clotting and fibrinolytic systems of plasma. Additionally, the vascular endothelium plays an important role in inflammation and tissue repair. Two principal modes of endothelial behavior may be differentiated, best defined as an antithrombotic state and as a prothrombotic state. Under typical physiological conditions, the endothelium mediates vascular dilatation (formation of NO, PGI2, adenosine, hyperpolarizing factor), prevents platelet adhesion and activation (production of adenosine, NO and PGI2, removal of ADP), blocks thrombin formation (tissue factor pathway inhibitor, activation of protein C via thrombomodulin, activation of antithrombin III) and mitigates fibrin deposition (t- and scuplasminogen activator production). Adhesion and transmigration of inflammatory leukocytes are attenuated, e.g., by NO and IL-10, and oxygen radicals are efficiently scavenged (urate, NO, glutathione, SOD; see, e.g., Becker, B F et al., Z. Kardiol 2000; 89(3):160-167).

When the endothelium is physically disrupted or functionally perturbed by postischemic reperfusion, acute and chronic inflammation, atherosclerosis, diabetes and chronic arterial hypertension, then opposing actions pertain. This prothrombotic, proinflammatory state is characterized by vaso-constriction, platelet and leukocyte activation and adhesion (externalization, expression and upregulation of von Willebrand factor, platelet activating factor, P-selectin, ICAM-1, IL-8, MCP-1, TNF alpha, etc.), promotion of thrombin formation, coagulation and fibrin deposition at the vascular wall (expression of tissue factor, PAI-1, phosphatidyl serine, etc.) and, in platelet-leukocyte coaggregates, additional inflammatory interactions via attachment of platelets to endothelial, monocyte and B-cell CD154.

The role of endothelial inflammation in the progression of atherosclerosis has been shown (Libby, P et al., in *Atherosclerosis and Coronary Artery Disease*, Fuster V, et al, eds. Lippincot-Raven, Philadelphia. 585-594 (1996); R. Ross, New Eng. J. Med.; 340:115-126 (1999)), and this has lead to efforts directed towards understanding the inflammatory factors responsible for lesion progression and identifying agents to regulate the inflammatory response.

CD40 is a 45-50 kD transmembrane glycoprotein found on many vascular cells (Hollenbough, D, J. Exp. Med. 282:33 (1995)), including B lymphocyte lineage cells. CD40 is a member of the TNF receptor family and has homology to the receptors for nerve growth factor, TNF-alpha, Fas and CD30. CD40 has been shown to play an important role in B cell differentiation and activation. Its primary role on immune cells is to enhance their activation and hence their production of cytokines and immunomodulatory molecules. Recently, CD40 has also been detected on human fibroblasts. An emerging view of the fibroblast is that it is far more than a structural cell, being capable of intimate interaction with cells of the immune system. In fibroblasts from several tissues, the engagement of CD40 with its ligand resulted in the secretion of proinflammatory molecules such as interleukin-6 (IL-6) and IL-8.

The ligand for CD40 is CD154 (also known as CD40 Ligand, CD40L and gp 39). CD154 is a membrane protein in the TNF family, and is a potent proinflammatory factor originally identified in CD4$^+$ T lymphocytes. CD154 was identified as a factor responsible for immunoglobulin isotype switching (Gordon, J, Eur. J. Immunol. 17:1535 (1987)). As expressed on activated T cells, it is a type II membrane protein (N-terminus intracellular and C-terminus extracellular) cells. The human CD154 protein is 261 residues long and has a single N-linked carbohydrate moiety.

Previous studies have established that CD154 is rapidly released after T cell activation (Graf, D, Eur. J. Immunol. 25:1749 (1995)), creating an 18 kDa hydrolytic product capable of inducing B cell proliferation (Pietravalle, F J. Biol. Chem., 271:5965 (1996)) and an inflammatory response in vascular cells (Schonbeck, 1997). Mutations in the CD154 gene are associated with a rare immunodeficiency state, X-linked hyper IgM syndrome (XLHIGM).

Antibodies to CD154 have been shown to suppress T cell and antibody mediated immune responses in a number of experimental systems. These include inhibition of graft rejection and blocking autoirunmune disorders (Durie, F H et al., Science, 261:1328 (1993)). The combined use of anti-CD154 antibodies and CD28 blockers (i.e., CTLA-4Ig) has been shown to be effective in blocking graft rejection in both murine and rhesus transplant models (Larsen, C P et al., Nature, 381: 434 (1996); Kirk, A D, Proc. Natl. Acad. Sci. (USA), 94:8789(1997)). Other studies have shown that the use ofanti-CD154 antibody as a single agent in rhesus kidney allografts has shown that this treatment is remarkably efficacious (Kirk, A D et al., Nature Medicine 5: 686. (1999)). Clinical studies are believed to be underway, using anti-CD154 humanized antibodies for treatment of lupus or other autoimmune disease.

CD154 is also known to be a key mediator of atherosclerotic lesion progression. This role of CD154 in atherosclerosis has been established by studies showing that CD154 antibodies (Mach, F, Nature, 394:200 (1998)) or CD154 gene targeting (Lutgens, E, Nature Medicine, 5:1313 (1999)) reduce atherosclerotic lesion development in the apo E-/- mouse.

Aukrust, et al. (Circulation; 100(6):614-620 (1999)), showed that a soluble form of CD154 was generated in patients with acute coronary thrombotic syndromes (eg., with unstable angina, or undergoing angioplasty and that the soluble CD154 was inflammatory to peripheral blood monocytes. From these observations, it was postulated that the soluble CD154 thus generated may trigger and/or propagate acute coronary syndromes.

CD154 is now known to reside in many cells within the vasculature, including platelets (Mach, F., Proc. Natl. Acad. Sci. (USA), 94:1931 (1997)); Banchereau, Ann Rev. Irrununol. 12:881 (1994)). Henn, et al., who showed that while CD154 was not exposed on the surface of unstimulated, discoid platelets, it rapidly became exposed on platelets during thrombin-induced aggregation, established the platelet location of CD154 in a pioneering study.

Phipps et al. (The Lancet, 357:2023-2024 (2001)) further elucidated that platelet soluble CD40 ligand is the cause of febrile responses and that keeping the release of CD40 ligand to a minimum or removing free CD40 ligand before transfusion may effectively reduce adverse events after platelet transfusion.

Eliopoulos et al. (Molecular Cell Biology, 20(15):5503-5515 (2000)) found that CD154 induced apoptosis through CD40 in carcinoma cells and identified a proapoptotic mechanism which depends on the endogenous production of cytotoxic cytokines and autocrine or paracrine induction of cell death.

There exists a need for therapeutic agents that can reduce the contributions made by platelets, via CD154/CD40 interactions, to atherosclerosis and other acute coronary syndromes. Furthermore, in view of the pro-inflammatory role of CD154, and given the potential therapeutic results of inhibiting the activity and effects of CD154, it would be desirable to have high affinity and high specificity inhibitors of this molecule.

Therapeutic agents directed to the prevention or reduction of platelet aggregation are known. For example, it has been suggested that administering a metalloproteinase inhibitor can reduce or block platelet aggregation. Certain other platelet blocking agents are directed against the platelet glycoprotein IIb-IIIa receptor that is involved in platelet aggregation. Large, randomized clinical trials have established that the three parenteral GPIIb-IIIa antagonists (abciximab, aggrastat and eptifibatide (INTEGRILIN®; Millennium Pharmaceuticals, Inc.)) reduce the incidence of acute coronary thrombosis in the settings of percutaneous interventions and unstable angina (Topol, E., Circulation, 97, 211 (1998)). One additional, unexpected benefit of this class of drugs is that they also augment the anticoagulant activity of heparin. It has been suggested that the drugs achieve this benefit, perhaps because they limit the expression of prothrombinase found on aggregated platelets and/or because they inhibit the binding of prothrombin to GP IIb-IIIa. Another unexpected benefit of this class of drugs is that they augment clot lysis by thrombolytics, perhaps because they inhibit platelet aggregation created by the prothrombotic environment created by fibrinolysis.

While these agents are beneficial to certain patients in these settings, further progress must be made toward improving treatment outcomes. Angioplasty, for example, has been shown to benefit patients, however the procedure is not without its adverse effects and complications. Recent clinical data from patients with vascular disease suggest that outcomes are not as good when inflammation is elevated as they are in patients without signs of inflammation. Despite a long-felt need to understand and discover methods for regulating thrombosis and inflammation, the complexity of the cellular interactions has complicated the development of completely satisfactory, safe and efficacious products and processes for regulating hemostatic function. As such, there remains a need for products and processes that permit the implementation of predictable controls of vascular inflammation and thrombosis, thus enabling the treatment of various diseases that are caused by undesired cellular function.

SUMMARY OF THE INVENTION

The present invention relates to compounds that are capable of specifically modulating CD154 mobilization and that are useful for stabilizing the thrombotic process and reducing the activation of cells involved in an inflammatory response.

It has been found that CD154 circulating in the vasculature is found on platelets. The present invention arose from efforts to understand the conditions required for the inflammatory activity of platelet CD154. The present invention inventors discovered that CD154 is indeed expressed on the surface of stimulated platelets, and that subsequent platelet aggregation (requiring the binding of fibrinogen to the platelet glycoprotein GP IIb-IIIa) caused the cleavage of CD154, resulting in the appearance of a soluble, 18-kDa fragment of the protein ("sCD154") capable of inducing an inflammatory response in endothelial cells. A recombinant form of sCD154 was made and has been shown that it is also pro-inflammatory.

Importantly, CD154 was discovered to be involved in thrombosis, not just inflammation, and that CD154 antagonists are desirable antithrombotics. It has also been discovered that inhibitors of CD154 hydrolysis are desirable as antithrombotics.

One aspect of the invention relates to metalloproteinase inhibitors that block the hydrolysis of CD154 upon platelet stimulation, and that metalloproteinase inhibitors are desirable antithrombotics and anti-inflammatory agents.

Another aspect of the invention relates to the treatment of platelets for transfusion with metalloproteinase inhibitors to treat or prevent inflammation and to enhance the viability of platelets following transfusion.

Another aspect of the invention relates to methods for the treatment of inflammation and/or thrombotic conditions, comprising the administration of CD154 antagonists, agents that inhibit CD154 hydrolysis, or metalloproteinase inhibitors. These methods, optionally provide for administration of additional agents that block platelet aggregation or enhance thrombolysis. These agents may be delivered by a variety of means, including local delivery, by incorporation into shaped or implanted articles, or may be delivered systemically such as by transdermal patch, intravenous administration or oral dosage forms.

The invention therefore concerns methods for modulating the mobilization of CD154 from platelets, comprising the administration of a platelet aggregation inhibitor. Another aspect of the invention relates to methods for modulating the mobilization of CD154 from platelets, comprising the administration of a platelet aggregation inhibitor. It has been found that INTEGRILIN® (eptifibatide; Millennium Pharmaceuticals, Inc.) and other GP IIb-IIIa antagonists, which inhibit platelet aggregation, blocked cleavage and release of the sCD154 protein even when platelets were stimulated by potent stimuli such as thrombin or TRAP.

Surprisingly, it has been found that these platelet aggregation inhibitors, delivered at suitably low doses, promote the mobilization of soluble CD154, leading to a pro-inflammatory and/or pro-thrombotic effect. The present invention provides methods for the treatment of patients having impaired immune systems, or whose immune systems are slow to mount a sufficient response to a given level of stimulus, comprising the administration of a platelet aggregation inhibitor at a dose selected to optimize the pro-inflammatory effects which are desired for those patients.

Another aspect of the present invention is the discovery that low doses of agents which only partially block platelet activation, aggregation, or the mobilization of CD154 from platelets, will potentiate the release of platelet CD154. In vivo or in vitro administration of an antithrombotic agent at a dosage level that is low enough to permit the continued progress of thrombosis, has been discovered to result in enhanced mobilization of CD154 from the platelet, leading to increased inflammation. In patients, increased inflammation correlates to some extent with worsened patient outcomes. In certain embodiments of the present invention, for example those related to the treatment of vascular or inflammatory disease, the present invention provides methods comprising the measurement of the levels of CD154 or sCD154 in a patient sample, and the use of these measurements to determine an initial dosage plan for the administration of antithrombotic medication, and for assessment of the sufficiency of a dosage level of antithrombotic or anti-inflammatory medication which has been administered. The present invention also relates to methods of treatment of cancer, immune system disorders, and thrombotic or inflammatory conditions with agents that modulate the mobilization of CD154 from platelets.

Another aspect of the present invention relates to the use of analytical methods to identify compounds suitable to modulate the release of CD154 from platelets. Suitable compounds are provided, including known and unknown, oral and parenteral, platelet glycoprotein GP IIb-IIIa antagonists that have the unexpected ability to modulate the release of soluble proinflammatory mediators, even when platelets are stimulated by potent agonists. The present invention also provides new uses for the platelet glycoprotein IIb-IIIa class of drugs, namely of limiting the extent of inflammation created by acute coronary thrombosis. In some aspects, the present invention provides for novel formulations of therapeutic anti-thrombotic, thrombolytic, or other agents, which are characterized by their ability to release the therapeutic agent at a rate and level which optimize their desired thrombosis inhibiting effects. In other aspects, novel therapeutic agents are provided, having characteristic pharmacokinetic profiles that optimize their desired pro-inflammatory or anti-inflammatory effects.

In certain aspects of the present invention, a variety of therapeutic agents that reduce platelet activation and/or platelet aggregation are used as anti-inflammatory agents. The particular therapeutic agent selected for use in the methods of the present invention is chosen on the basis of the relevant clinical setting and desired therapeutic profile. It has been shown, for example, that aspirin blocks release of CD154 from platelets in circumstances when collagen is the agent causing platelet activation, but aspirin does not block CD154 release in circumstances where ADP is the platelet agonist. It is presently believed that this difference is attributable to aspirin's mechanism of action, involving blockage of Thromboxane $A_2$. It is possible, therefore, that aspirin administered by itself might be a more effective anti-inflammatory agent in patients whose disorders involve inflammatory processes which are collagen-mediated, rather than in patients having thrombotic disorders of different etiology. These latter patients are likely to be more beneficially treated by administration of aspirin, if aspirin is desired, in combination with other therapeutic agents. Therefore, the present invention relates to methods for selection of a treatment regime for a patient, comprising the steps of evaluating the inflammatory mediators involved in the patient's condition to be treated, identifying the anti-thrombotic and/or inflammatory agents which impact those inflammatory mediators in the desired fashion, and determining the appropriate dosage level of those agents, and planning a treatment regime involving the administration of an anti-thrombotic agent in combination with at least one additional therapeutic agent, which may be an anti-inflammatory agent, a thrombolytic, an anti-cancer drug, or any other therapeutic agent directed to the condition to be treated.

In some aspects of the invention, therapeutic agents are selected based on their differential abilities to act acutely and/or locally. In other aspects, therapeutic agents are selected to optimize a preferred indirect or systemic action.

The present invention permits the tailoring of a therapeutic candidate to the particular therapeutic indication more precisely than has been possible in the past. For example, the compounds and methods of the present invention are adaptable for numerous intervention points in the path from platelet formation to release of soluble platelet CD154. Agents may be chosen with direct impact only on CD154, such as those that prevent the cleavage or release of CD154 from the platelet surface. Gene therapy introduction of modified, inactivated CD154 constructs are contemplated in the present invention. Anti-sense nucleic acids constructs are also intended, and are known in the literature.

The present invention also provides solutions to the complex problem of identifying regulatory compounds that can be used to regulate cellular function, including CD154 regulation activity. Despite the complexity of signal transduction networks in cells, the present invention provides for an efficient method for regulating CD154 activity and identifying compounds capable of specifically regulating CD154 activity.

The present invention is particularly advantageous because it provides for a method to identify compounds that can regulate the production of IgM or IgE by an animal without substantially interfering with the production of IgG and IgA by an animal. As such, unlike traditional immunosuppressive reagents, which suppress an animal's immune response indiscriminately, a compound identified by a method of the present invention enables an animal to mount an immune response against foreign pathogens by producing IgG and IgA antibodies. Thus, persons of skill in the art will immediately recognize the advantages arising from the present invention, which include the identification and uses of compounds that are useful for the treatment of allergic and autoimmune diseases but are not disruptive to an animal's overall immune response.

Another aspect of the present invention relates to a method to identify a compound that controls CD154 regulation activity in a cell, comprising: (1) contacting a cell with a putative regulatory compound, wherein the cell includes a CD154 protein; and (2) assessing the ability of the putative regulatory compound to regulate the activity of the CD154. Another embodiment of the present invention includes a method to identify a compound that controls CD154 regulation of activity in a cell, comprising: (1) contacting a cell with a putative regulatory compound, wherein the cell includes CD40 protein; and (2) assessing the ability of the putative regulatory compound to regulate the activity of the CD154 protein. In particular, these methods of the present invention include a step of stimulating the cell, prior to the assessing step, with CD154.

Also included in the present invention is a regulatory compound identified by said compound's ability to regulate a biological function selected from the group consisting of immunoglobulin heavy chain class switching, cytokine production and inflammatory cell activation, the compound being capable of penetrating the plasma membrane of a cell and of inhibiting the ability of CD154 protein to regulate inflammatory activity.

Another aspect of the present invention relates to a method to inhibit immunoglobulin heavy chain class switching, comprising inhibiting the activity of CD154 protein. The present invention also includes a method to inhibit cytokine production by a cell having CD154, comprising inhibiting the activity of a CD154 protein.

Still another aspect of the present invention includes a method to treat an animal with a disease selected from the group consisting of a disease involving an allergic response, and an autoimmune disease, said method comprising administering to an animal an effective amount of a therapeutic composition comprising a compound that modulates or controls CD154 regulation activity.

Another aspect of the present invention includes a kit to identify compound that controls CD154 regulation of inflammatory activity in a cell, the kit comprising: (1) a cell comprising or expressing a CD154 protein; and (2) a means for detecting regulation of the CD154 protein.

Other aspects, objects, features and advantages of the present invention would be apparent to one of ordinary skill in the art from the following detailed description illustrating the preferred embodiments of the invention.

BRIEF DESCRIPTION OF THE DRAWINGS

FIG. 1 shows results of an experiment conducted with a perfusion chamber showing a reduced mean thrombus height in CD40L-/- mice at 3200/s.

DETAILED DESCRIPTION OF THE INVENTION

Figure 2:
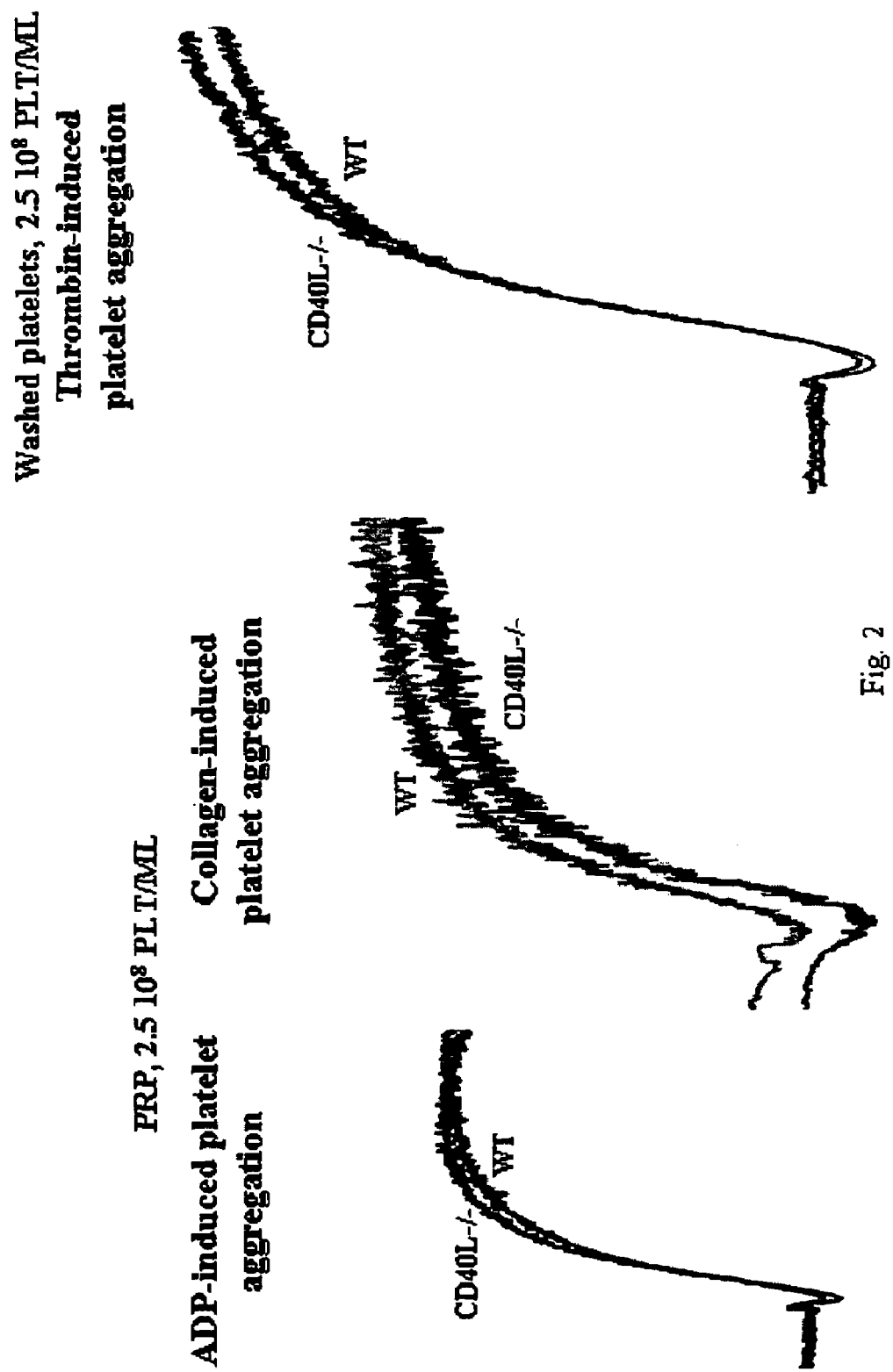
FIG. 2 shows a comparison of platelet aggregation induced by ADP, collagen and thrombin in a treated population.

The present invention relates to compounds that are capable of modulating CD154 mobilization and that are useful for stabilizing the thrombotic process and reducing the activation of cells involved in an inflammatory response.

Certain aspects of the present invention are directed to methods and compositions that have antithrombotic effects through inhibition of the activity of the CD154 ordinarily expressed on platelets. This inhibition may be accomplished by intervention in a variety of steps, as described herein.

In another embodiment, CD154 inhibitors or agents that decrease the release of CD154, such as metalloproteinase inhibitors, are useful in the present invention for the treatment of platelets used in patient transfusions. Platelets are used in the treatment of patients for a variety of conditions including, but not limited to hemophilia, other blood disorders and chemotherapy. Platelets used for transfusion are typically harvested from peripheral blood, either blood from allogeneic donors or autologous blood from the patient, separated from other blood products and placed in storage at about 22-37° C., preferably about 24° C. for up to about 5 days. During storage, platelets are continually agitated in order to prevent clotting prior to use. It has been noted in the art that platelet transfusion patients are sometimes afflicted with an inflammatory response in association with the transfusion. The inventors have discovered that during storage platelets release significant amounts of soluble CD154. As stated previously, CD154 is involved in both thrombosis and inflammation. Metalloproteinase inhibitors inhibit the release of soluble CD154 from platelets. It is therefore an aim of the present invention to provide compositions and methods for the treatment of platelets used in transfusion in order to prevent and/or treat inflammation in platelet transfusion patients and to enhance the viability of platelets, following transfusion.

It is a preferred embodiment that platelets be incubated with an effective amount of a metalloproteinase inhibitor during storage in order to inhibit the release of soluble CD154 and the formation of thrombi prior to administration to a recipient. It is a further preferred embodiment that platelets be treated with an effective amount of a metalloproteinase inhibitor to inhibit release of soluble CD154 from the platelets prior to administration to the recipient. It is yet a further preferred embodiment to administer an effective amount of a metalloproteinase inhibitor directly to a platelet transfusion recipient in association with said platelet transfusion. Said administration of metalloproteinase inhibitor to said recipient can occur prior to, concurrent with, or subsequent to said transfusion of platelets to said recipient. In the case of concurrent administration of metalloproteinase inhibitor and platelets, said administration of metalloproteinase inhibitor can be in the same or in a separate composition as the composition containing said platelets.

In the case of direct administration of metalloproteinase inhibitor to the platelet transfusion recipient, administration of an effective amount of metalloproteinase inhibitor to prevent or treat inflammation or thrombus formation can be via a single dose or via multiple administrations of divided doses. Further, direct administration of metalloproteinase inhibitor to a patient can include a therapeutic profile having quick onset of the effective dose and a release formulation that permits steady release. It is further contemplated that the treatment of platelets with metalloproteinase inhibitor can be accomplished using any one of these methods or any combination thereof.

It is understood that any metalloproteinase inhibitor suitable for administration to patients can be used in this method. Preferred are those metalloproteinase inhibitors that have been approved or indicated for human use. Metalloproteinase inhibitors include HONHCOCH$_2$CH(CH$_2$CH(CH$_3$)$_2$—CO—NaI-Ala-NHCH$_2$CH$_2$NH$_2$ (TAPI-I), tissue inhibitor of metalloprotease-2 (TIMP-2), doxycycline, galardin, and SB-3CT(MMP2 MMP9 inhibitor VI) and the like which are well known to one of ordinary skill in the art. Most preferred metalloproteinase inhibitors include galardin, doxycycline, TAPI-1 or TIMP-2. Metalloproteinase inhibitors can be used singly or in combination with one another in the method of the present invention.

It is further contemplated that treatment of platelets with a metalloproteinase inhibitor can include treatment of the patient with at least one additional agent which blocks platelet aggregation or which enhances thrombolysis. An example of such an additional agent which blocks platelet aggregation is a platelet glycoprotein GP IIb-IIIa antagonist, such as INTEGRILIN® (eptifibatide; Millennium Pharmaceuticals, Inc.).

Certain preferred embodiments of the invention utilize metalloproteinase inhibitors for the treatment of thrombosis and/or inflammation, in view of the role we have discovered that is played by metalloproteinases in the cleavage of soluble CD154 from the platelet. In particularly preferred embodiments, metalloproteinase inhibitors are administered for the prevention and treatment of inflammatory disorders, such as arthritis, multiple sclerosis, inflammatory bowel syndrome, organ or tissue transplant, graft vs. host mediated disorders, stroke, and Crohn's disease. Particularly preferred are agents that share certain biological functions of TAPI, a metalloproteinase inhibitor, which blocks the hydrolysis of CD154. Other desirable therapeutic agents utilized in the present invention are inhibitors of enzymes whose expression is increased in vascular disorders, such as gelatinase-A (also known as matrix metalloproteinase-2, MMP-2 or type IV collagenase). Desirable therapeutic candidates of the present invention include inhibitors of other proteolytic enzymes selected from the group involved in remodeling the extracellular matrix or with extracellular matrix turnover, such as serine proteinases of the plasminogen system and matrix metalloproteinases (MMPs). Many agents which have these desirable effects are described in the literature, and include, by way of example and not limitation, anti-gelatinase-A antibodies, the recombinant human-tissue inhibitor of metalloproteinases-2 (TIMP-2), soluble or recombinant forms of endogenous human serine proteinases or matrix metalloproteinases, and selective inhibitors of metalloproteinases such as phenanthroline and SC44463 (See, e.g. Sawicki G. et al., Nature, 386:616-619 (1997); Kazes et al., Blood, 96, 9:3064-3069, (2000)). Other therapeutic agents contemplated by the present invention are the metalloproteinases that release members of the tumor necrosis factor family from their cell-membrane bound precursors (see e.g., Black et al., Nature, 385:729-733 (1997); Moss et al., Nature, 385:733-736 (1997)).

Modified or inactivated soluble CD154 are also desirably administered in the present invention, to compete with the active forms of CD154 that may be released from platelets. In other aspects, an anti-CD154 antibody is administered, selected for a desired profile of anti- or pro-thrombotic activity as well as its anti-CD154 characteristics.

In an embodiment of the present invention, related to the treatment of stroke or other cerebrovascular disorders, the therapeutic candidate is selected to optimize activities directed to reduction of CD154 release, in distinction from a therapeutic profile that also involves anti-platelet intervention with greater anti-thrombotic effects.

Agents that interfere with the binding of CD154 with CD40 by acting on the CD40 binding site are also contemplated in the present invention, such as anti-CD40 antibodies and the like. Methods are provided for modulating the thrombotic effect of CD40, comprising the administration of a CD40 antagonist, alone or in conjunction with another therapeutic agent.

In yet other embodiments of the present invention, therapeutic agents are selected which selectively block only one of platelet activation, or platelet aggregation, or the expression of CD154 by the platelet. In more particularly preferred embodiments of the present invention, the therapeutic candidate is tailored to selectively block only one particular mechanism for activation of platelets. Tailoring the precise point of intervention in the path from platelet aggregation through activation to expression and release of soluble CD154 permits the selection of different characteristic for acute-phase treatments then would be desirable for a chronic treatment, and vice versa. For many of the embodiments of the present invention, the desirable therapeutic profile includes quick onset of the effective dose, and a release formulation that permits steady release. The objective of therapeutic candidate selection dosage is to quickly achieve the effective therapeutic range, and then maintain it. The present invention provides methods of treatment comprising the identification of the desirable therapeutic profile of a CD154 antagonist, alone or in combination with other therapeutic agents.

In other embodiments of the present invention, agents that are known to block the inflammatory activities of CD154 are used for their unexpected anti-thrombotic benefits. Anti-CD154 antibodies are preferred embodiments of this aspect of the invention.

The invention provides methods for the administration of antithrombotic agents in a course of treatment including immunosuppressive therapy, to reduce the potential effect of soluble CD154 during antithrombotic therapy. Similar immunosuppression is desirable in certain anti-cancer and other therapeutic indications described herein.

In further embodiments of the present invention, antithrombotic agents are administered during times of vascular surgery, injury or disease, to reduce the inflammatory complications of the vascular injury or intervention. These agents may be administered alone or in combination with other therapeutic agents that block the release of soluble CD154, such as during coronary artery bypass surgery, to lessen the complications of the bypass surgery, which are mediated by inflammatory factors.

The present invention provides methods for identifying compounds that modulate CD154 regulation activity and products identified using such methods. As used herein, the phrase "signal transduction pathway" refers to at least one biochemical reaction, but more commonly a series of biochemical reactions, which result from interaction of a cell with a stimulatory compound. The interaction of a stimulatory compound with a cell generates a "signal" that is transmitted through a signal transduction pathway, ultimately resulting in CD154 activation. Compounds inhibitory to signal transduction pathways (antagonists) are also useful and can be identified by the methods of the present invention.

A signal transduction pathway of the present invention can include a variety of signal transduction molecules that play a role in the transmission of a signal from one portion of a cell to another portion of a cell. As used herein, the term "molecule" refers to a protein, a lipid, a nucleic acid or an ion, and at times is used interchangeably with such terms. In particular, a signal transduction molecule refers to a protein, a lipid, a nucleotide, or an ion involved in a signal transduction pathway. Signal transduction molecules of the present invention include, for example, cell surface receptors and intracellular signal transduction molecules. As used herein, the phrase "cell surface receptor" includes molecules and complexes of molecules capable of receiving a signal and the transmission of such a signal across the plasma membrane of a cell. The phrase "intracellular signal transduction molecule," as used herein, includes those molecules or complexes of molecules involved in transmitting a signal from the plasma membrane of a cell through the cytoplasm of the cell, and in some instances, into the cell's nucleus. The phrase "stimulatory compound", as used herein, includes ligands capable of binding to cell surface receptors to initiate a signal transduction pathway, as well as intracellular initiator molecules capable of initiating a signal transduction pathway from inside a cell.

The present invention method can further comprise assessing the ability of a putative CD154 inhibitor to inhibit: immunoglobulin heavy chain class switching in a cell; cytokine production by a cell; or activation of inflammatory cells (i.e., cells involved in an inflammatory response). Methods for determining immunoglobulin heavy chain class switching are to those of skill in the art. For example, Southern blots can be performed using DNA probes specific for genes encoding different classes of immunoglobulin heavy chains to look for rearrangement of the DNA encoding the different classes. Alternatively, immunoassays can be performed on proteins produced by the treated cell using antibodies specific for different classes of immunoglobulin heavy chains. Methods for determining cytokine production are known to those of skill in the art. For example, cell responsiveness assays using cells capable of responding to a cytokine can be used to test the disruption of cytokine production by a putative regulatory compound. In addition, immunoassays using antibodies specific for a cytokine can be used to test the disruption of cytokine production by a putative regulatory compound. Methods for determining inhibition of inflammatory cell activation are known to those of skill in the art by testing the ability of an inflammatory cell to perform a desired biological function in the presence or absence of a putative regulatory protein.

Suitable cells for use with the present invention include any cell that has CD154 protein. Such cells can include normal cells or transformed cells (i.e., with a heterologous nucleic acid molecule) that express CD154 in a native physiological context (e.g. Pre-B cells, B lymphocytes, cancer cells, fibroblasts, Langerhans cells, epithelial cells monocytes and dendritic cells). Alternatively, cells for use with the present invention can include spontaneously occurring variants of normal cells, or genetically engineered cells, that have altered signal transduction activity, such as enhanced responses to particular ligands. Signal transduction variants of normal cells can be identified using methods known to those in the art. For example, variants can be selected using fluorescence activated cell sorting (FACS) based on the level of calcium mobilization by a cell in response to a ligand. Genetically engineered cells can include recombinant cells of the present invention (described in detail below) that have been transformed with, for example, a recombinant molecule encoding a signal transduction molecule of the present invention.

Cells for use with the present invention include mammalian, invertebrate, plant, insect, fungal, yeast and bacterial cells. Preferred cells include mammalian, amphibian and yeast cells. Preferred mammalian cells include primate, non-human primate, mouse and rat, with human cells being most preferred.

In one embodiment, a cell suitable for use in the present invention has a functional CD154 on the surface of the cell. A functional CD154 can comprise a full-length or a portion of a CD154 that is capable of transmitting a signal across the plasma membrane of a cell, upon ligation with an anti-CD154 antibody or a CD154, in such a manner that immunoglobulin heavy chain class switching results. Preferably, a cell of the present invention expresses a CD154 derived from a human, mouse or rat, with human cells being preferred.

In another embodiment, a cell suitable for use in the present invention has one or more intracellular signal transduction molecules capable of transmitting a signal through the cytoplasm of the cell, resulting in CD154 activation. An intracellular signal transduction molecule as described herein can be produced in a cell by expression of a naturally occurring gene and/or by expression of a heterologous nucleic acid molecule transformed into the cell.

Signal transduction molecules referred to herein include the natural full-length protein, or can be a functionally equivalent protein in which amino acids have been deleted (e.g., a truncated version of the protein), inserted, inverted, substituted and/or derivatized (e.g., phosphorylated, acetylated, glycosylated, carboxymethylated, myristoylated, prenylated or palmitoylated amino acids) such that the modified protein has a biological activity and/or function substantially similar to that of the natural protein. Modifications can be accomplished by techniques known in the art, including, but not limited to, direct modifications to the protein or modifications to the gene encoding the protein. Such modifications to the gene encoding the protein can include using, for example, classic or recombinant DNA techniques to effect random or targeted mutagenesis (see, for example, Sambrook et al., Molecular Cloning: A Laboratory Manual, Cold Spring Harbor Labs Press, 1989, which is incorporated herein by reference in its entirety).

Functionally equivalent proteins can be selected using assays established to measure the biological activity of the protein. For example, a functionally equivalent cell surface receptor would have a similar ability to bind a particular ligand, as would the corresponding natural cell surface receptor protein. As a further example, a functionally equivalent intracellular signal transduction protein would have a similar ability to associate with and regulate the activity of another intracellular molecule as would the corresponding natural intracellular signal transduction protein.

In certain embodiments, a cell of the present invention is transformed with at least one heterologous nucleic acid molecule. A nucleic acid molecule as described herein can be DNA, RNA, or hybrids or derivatives of either DNA or RNA. Nucleic acid molecules as referred to herein can include regulatory regions that control expression of the nucleic acid molecule (e.g., transcription or translation control regions), full-length or partial coding regions, and combinations thereof. It is to be understood that any portion of a nucleic acid molecule can be produced by: (1) isolating the molecule from its natural milieu; (2) using recombinant DNA technology (e.g., PCR amplification, cloning); or (3) using chemical synthesis methods. A gene includes all nucleic acid sequences related to a natural cell surface receptor gene such as regulatory regions that control production of a cell surface receptor encoded by that gene (such as, but not limited to, transcription, translation or post-translation control regions) as well as the coding region itself.

A nucleic acid molecule can include functional equivalents of natural nucleic acid molecules encoding a protein. Functional equivalents of natural nucleic acid molecules can include, but are not limited to, natural allelic variants and modified nucleic acid molecules in which nucleotides have been inserted, deleted, substituted, and/or inverted in such a manner that such modifications do not substantially interfere with the nucleic acid molecule's ability to encode a molecule of the present invention. Preferred functional equivalents include sequences capable of hybridizing under stringent conditions (i.e., sequences having at least about 70% identity), to at least a portion of a signal transduction protein encoding nucleic acid molecule according to conditions described in Sambrook et al., ibid.

As guidance in determining what particular modifications can be made to any particular nucleic acid molecule, one of skill in the art should consider several factors that, without the need for undue experimentation, permit a skilled artisan to appreciate workable embodiments of the present invention. For example, such factors include modifications to nucleic acid molecules done in a manner so as to maintain particular functional regions of the encoded proteins including, a ligand binding site, a target binding site, a kinase catalytic domain, etc. Functional tests for these various characteristics (e.g., ligand binding studies and signal transduction assays such as kinase assays, and other assays described in detail herein and those known by those in the art) allows one of skill in the art to determine what modifications to nucleic acid sequences would be appropriate and which would not.

Transformation of a heterologous nucleic acid molecule (e.g., a heterologous cell surface receptor encoding a nucleic acid molecule) into a cell suitable for use in the present invention can be accomplished by any method by which a gene is inserted into a cell. Transformation techniques include, but are not limited to, transfection, retroviral infection, electroporation, lipofection, bacterial transfer and spheroplast fusion. Nucleic acid molecules transformed into cells suitable for use in the present invention can either remain on extra-chromosomal vectors or can be integrated into the cell genome.

Expression of a nucleic acid molecule of the present invention in a cell can be accomplished using techniques known to those skilled in the art. Briefly, the nucleic acid molecule is inserted into an expression vector in such a manner that the nucleic acid molecule is operatively joined to a transcription control sequence in order to be capable of effecting either constitutive or regulated expression of the gene when the gene is transformed into a host cell. Construction of desired expression vectors can be performed by methods known to those skilled in the art and expression can be in eukaryotic or prokaryotic systems. An expression system can be constructed from control elements, including transcription control sequences, translation control sequences, origins of replication, and other regulatory sequences that are compatible with a host cell, operatively linked to nucleic acid sequences using methods known to those of skill in the art. (see, for example, Sambrook et al., ibid.).

In one embodiment, a cell suitable for use in the present invention is transformed with a nucleic acid molecule encoding CD154, as described in detail herein.

It is within the scope of the present invention that a cell can be transformed with both a nucleic acid molecule encoding at least one type of signal transduction molecule and a nucleic acid molecule encoding at least one type of cell surface receptor.

In one embodiment, the method of the present invention comprises contacting a cell with a putative regulatory compound. According to the present invention, putative regulatory compounds include compounds that are suspected of being capable of regulating CD154 activity. The term "activity" refers to any stage of activation of a signal transduction molecule by, for example, conformational change of a molecule which results in the acquisition of catalytic activity by the molecule; the phosphorylation of a molecule, thereby resulting in the acquisition or loss of catalytic activity by the molecule; or the translocation of a molecule from one region of a cell to another, thereby enabling the molecule to bind another molecule. The term "regulate" refers to controlling the activity of a molecule and/or biological function, such as enhancing or diminishing such activity or function.

Putative compounds as referred to herein include, for example, compounds that are products of rational drug design, natural products and compounds having partially defined signal transduction regulatory properties. A putative compound can be a protein-based compound, a carbohydrate-based compound, a lipid-based compound, a nucleic acid-based compound, a natural organic compound, a synthetically derived organic compound, an anti-idiotypic antibody and/or catalytic antibody, or fragments thereof. A putative regulatory compound can be obtained, for example, from libraries of natural or synthetic compounds, in particular from chemical or combinatorial libraries (i.e., libraries of compounds that differ in sequence or size but that have the same building blocks; see for example, U.S. Pat. Nos. 5,010,175 and 5,266,684 to Rutter and Santi, which are incorporated herein by reference in their entirety) or by rational drug design.

In a rational drug design procedure, the three-dimensional structure of a compound, such as a signal transduction molecule can be analyzed by, for example, nuclear magnetic resonance (NMR) or x-ray crystallography. This three-dimensional structure can then be used to predict structures of potential compounds, such as putative regulatory compounds by, for example, computer modeling. The predicted compound structure can then be produced by, for example, chemical synthesis, recombinant DNA technology, or by isolating a mimetope from a natural source (e.g., plants, animals, bacteria and fungi). Potential regulatory compounds can also be identified using SELEX technology as described in, for example, PCT Publication Nos. WO 91/19813; WO 92/02536 and WO 93/03172 (which are incorporated herein by reference in their entirety).

In particular, a naturally occurring intracellular signal transduction molecule can be modified based on an analysis of its structure and function to form a suitable regulatory compound. For example, a compound capable of regulating CD154 can comprise a compound having similar structure to a selected number of residues of the amino terminus of CD154. Such a compound can comprise a peptide, a polypeptide or a small organic molecule.

Putative regulatory compounds can also include molecules designed to interfere with CD154. For example, mutant CD154 can be created that interfere with the coupling of the receptor to intracellular signal transduction proteins. Alternatively, mutant CD154 can be created that interfere with the binding of CD154 to CD40. Putative regulatory compounds can include agonists and antagonists of CD154. Such agonists and antagonists can be selected based on the structure of a naturally occurring ligand to CD40.

The conditions under which the cell of the present invention is contacted with a putative regulatory compound, such as by mixing, are conditions in which the cell can exhibit CD154 activity if essentially no other regulatory compounds are present that would interfere with such activity. Achieving such conditions is within the skill in the art, and includes an effective medium in which the cell can be cultured such that the cell can exhibit CD154 activity. For example, for a mammalian cell, effective media are typically aqueous media comprising RPMI 1640 medium containing 10% fetal calf serum.

Cells of the present invention can be cultured in a variety of containers including, but not limited to, tissue culture flasks, test tubes, microtiter dishes, and petri plates. Culturing is carried out at a temperature, pH and carbon dioxide content appropriate for the cell. Such culturing conditions are also within the skill in the art. For example, for Ramos cells, culturing can be carried out at 37° C., in a 5% $CO_2$ environment.

Acceptable protocols to contact a cell with a putative regulatory compound in an effective manner include the number of cells per container contacted, the concentration of putative regulatory compound(s) administered to a cell, the incubation time of the putative regulatory compound with the cell, the concentration of ligand and/or intracellular initiator molecules administered to a cell, and the incubation time of the ligand and/or intracellular initiator molecule with the cell. Determination of such protocols can be accomplished by those skilled in the art based on variables such as the size of the container, the volume of liquid in the container, the type of cell being tested and the chemical composition of the putative regulatory compound (i.e., size, charge etc.) being tested.

In one embodiment of the method of the present invention, a suitable number of cells are added to a 96-well tissue culture dish in culture medium. A preferred number of cells include a number of cells that enables one to detect a change in CD154 activity using a detection method of the present invention (described in detail below). A more preferred number of cells include between about 1 and 1×10<6> cells per well of a 96-well tissue culture dish. Following addition of the cells to the tissue culture dish, the cells can be pre-incubated at 37° C., 5% $CO_2$ for between about 0 to about 24 hours.

Putative regulatory compound(s) suspended in culture medium is added to the cells in an amount that is sufficient to regulate the activity of a CD154 protein in a cell such that the regulation is detectable using a detection method of the present invention. A preferred amount of putative regulatory compound(s) comprises between about 1 nM to about 10 mM of putative regulatory compound(s) per well of a 96-well plate. The cells are allowed to incubate for a suitable length of time to allow the putative regulatory compound to enter a cell and interact with a signal transduction molecule. A preferred incubation time is from about 1 minute to about 48 hours.

In another embodiment of the method of the present invention, cells suitable for use in the present invention are stimulated with a stimulatory molecules capable of binding to CD40 of the present invention to initiate a signal transduction pathway and create a cellular response. Preferably, cells are stimulated with a stimulatory molecule following contact of a putative regulatory compound with a cell. Suitable stimulatory molecules can include, for example, antibodies that bind specifically to the extracellular domain of CD154. Preferred stimulatory molecules include, but are not limited to, anti-human CD40 antibody G28-5, soluble CD154, membrane-bound CD154 (e.g., CD154 bound to the plasma membrane of a cell or CD154 incorporated into a synthetic lipid-based substrate such as a liposome or micelle) and mixtures thereof. A suitable amount of stimulatory molecule to add to a cell depends upon factors such as the type of ligand used (e.g., monomeric or multimeric; permeability, etc.) and the abundance of the receptor on a cell. Preferably, between about 1.0 nM and about 1 mM of ligand is added to a cell.

Soluble forms of CD154 can be expressed in known prokaryotic or eukaryotic systems, but preferably in mammalian cell cultures, as recombinant proteins and be purified from culture supernatants or cell digests by conventional methods. Apart from a possible direct therapeutic use of the soluble CD40 molecules, the latter can furthermore also be employed for the identification of other substances that block the interaction of membrane-associated CD154 and thus likewise have therapeutic potential. This can take place, for example, in cell-free receptor binding assays (EP-A-0 488 170) in which the soluble CD40 molecules are present on a solid phase, and the binding of soluble CD154s is followed by means of suitable labeling or antibodies. Assays of this type provide, because of the possibility of automating them, the means for investigating a large number of substances for their interaction with CD154/CD154s (receptor screening).

The methods of the present invention include determining if a putative regulatory compound is capable of regulating CD154 activation. Such methods include assays described in detail in the Examples section. The method of the present invention can further include the step of performing a toxicity test to determine the toxicity of a putative regulatory compound.

Another aspect of the present invention includes a kit to identify compounds capable of regulating CD40 regulation of inflammatory activity in a cell. Such a kit includes: (1) a cell comprising CD154 protein; and (2) a means for detecting regulation of CD154 protein. Such a means for detecting the regulation of CD154 protein include methods and reagents known to those of skill in the art, for example, CD154 activity can be detected using, for example, activation assays described in Example 2. Means for detecting the regulation of p38 MAPK protein, and indication of platelet activation also include methods and reagents known to those of skill in the art. Suitable cells for use with a kit of the present invention include cells described in detail herein. A preferred cell for use with a kit includes, a human cell.

The present invention also includes the determination as to whether a putative regulatory compound is capable of regulating a biological response in a mammal. Such a method entails administering a putative regulatory compound to an animal, such compound being shown, using an assay of the present invention, to regulate CD154 activity in a cell. Such a determination is useful for determining conditions under which a putative regulatory compound can be administered to an animal as a therapeutic composition. Thus, it is within the scope of the present invention that those conditions stated herein for testing a compound in an animal can be used when administering a therapeutic composition of the present invention. In particular, a putative regulatory compound can be administered to an animal to determine if the compound is capable of regulating, for example, an inflammatory response, a response to an infectious agent, an autoimmune response, a metabolic response, a cardiovascular response, an allergic response and/or an abnormal cellular growth response in the animal. Acceptable protocols to administer putative regulatory compounds to test the effectiveness of the compound include individual dose size, number of doses, frequency of dose administration, and mode of administration. Determination of such protocols can be accomplished by those skilled in the art. A suitable single dose is a dose that is capable of altering a biological response in an animal when administered one or more times over a suitable time period (e.g., from minutes to days over weeks). Preferably, a dose comprises from about 1 ng of the compound per kilogram of body weight (ng/kg) to about 1 gram of compound per kilogram of body weight (gm/kg), more preferably 100 ng/kg to about 100 milligrams/kilogram (mg/kg), and even more preferably from about 10 micrograms of compound per kilogram of body weight to about 10 mg/kg. Modes of administration can include, but are not limited to, aerosolized, subcutaneous, rectally, intradermal, intravenous, nasal, oral, transdermal and intramuscular routes.

A putative regulatory compound can be combined with other components such as a pharmaceutically acceptable excipient and/or a carrier, prior to administration to an animal. Examples of such excipients include water, saline, Ringer's solution, dextrose solution, Hank's solution, and other aqueous physiologically balanced salt solutions. Non-aqueous vehicles, such as fixed oils, sesame oil, ethyl oleate, or triglycerides may also be used. Other useful formulations include suspensions containing viscosity-enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, m- or o-cresol, formalin and benzyl alcohol. Standard formulations can either be liquid injectables or solids that can be taken up in a suitable liquid as a suspension or solution for injection. Carriers are typically compounds that increase the half-life of a compound in the treated animal. Suitable carriers include, but are not limited to, polymeric controlled release vehicles, biodegradable implants, liposomes, bacteria, viruses, oils, esters, and glycols. Preferred controlled release formulations are capable of slowly releasing a composition of the present invention into an animal. Suitable controlled release vehicles include, but are not limited to, biocompatible polymers, other polymeric matrices, capsules, microcapsules, microparticles, bolus preparations, osmotic pumps, diffusion devices, liposomes, lipospheres, and transdermal delivery systems. Other controlled release vehicles of the present invention include liquids that, upon administration to an animal, form a solid or a gel in situ. Preferred controlled release vehicles are biodegradable (i.e., bioerodible).

In another embodiment, the present invention includes conducting a toxicity test on an animal to determine the toxicity of a putative regulatory compound. Toxicity tests for putative regulatory compounds can be performed, for example, on animals after a putative regulatory compound has been determined to have an effect at the cellular level on signal transduction, such as the regulation of cellular inflammatory responses. Such toxicity tests are within the skill of the art, and generally involve testing the toxicity of a compound in vivo or in vitro. A suitable method for testing the toxicity of a putative regulatory compound in vivo can involve scientifically controlled administration of the putative regulatory compound to a number of animals and a period of observance in which the effects of the compound on various aspects of the animals biological functions (e.g., occurrence of tissue damage, functioning of organs and death) are noted. Suitable methods for testing the toxicity of a putative regulatory compound in vitro can involve scientifically controlled administration of the putative regulatory compound to a cell and subsequent measurement of cell function, cytotoxicity, or cell death. Cell function can be measured by any one of a wide range of assays, which will be apparent to one of skill in the art, several of which are herein disclosed (e.g., tyrosine phosphorylation, calcium mobilization and phosphoinositide assays). Methods to measure cytotoxicity are well known in the art and include measurement of the ability to reduce chromogenic substrates such as the tetrazolium-based MTT or sulphorhodamine blue, ATP-bioluminescence assays and fluorescence assays, for example using the Fluorescent Green Protein, among many other readily available assays (see, for example, Bellamy, Drugs 44(5):690-708, 1992, which is incorporated herein by reference in its entirety). Methods to measure cell death include, for example, Coomassie blue staining, acridine orange staining, terminal deoxynucelotidyl transferase (TDT) assays for measuring DNA fragmentation, neutral red exclusion, and measuring changes in forward light scattering in a flow cytometer.

The substantially pure proteins that have been expressed by methods of the present invention may be used in immunodiagnostic assay methods well known to those of skill, including radio-immunoassays (RIAs), enzyme immunoassays (EIAs) and enzyme-linked immunosorbent assays (ELISAs). The substantially pure proteins of the present invention, in soluble form, may be administered alone or in combination with other proteins of the present invention, or with other agents, including lymphokines and monokines or drugs, for the treatment of immune-related diseases and disorders in animals, including humans. As examples of such disorders that may benefit from treatment with the substantially pure proteins of the present invention may be mentioned immune deficiency diseases, diseases of immediate type hypersensitivity, asthma, hypersensitivity pneumonitis, immune-complex disease, vasculitis, systemic lupus erythematosus, rheumatoid arthritis, immunopathogenic renal injury, acute and chronic inflammation, hemolytic anemias, platelet disorders, plasma and other cell neoplasms, amyloidosis, parasitic diseases, multiple sclerosis, Guillain-Barre syndrome, acute and subacute myopathic paralysis, myasthenia gravis, immune endocrinopathies, and tissue and organ transplant rejection, all as described in Petersdorf et al., eds., Harrison's Principles of Internal Medicine, supra. See also Weir, ed., supra; Boguslaski et al., eds., supra; and Holborow et al., eds., supra.

When used for immunotherapy, the proteins of the present invention may be unlabeled or labeled with a therapeutic agent. Examples of therapeutic agents that can be coupled to the proteins of the invention for immunotherapy are drugs, radioisotopes, lectins, and toxins.

The dose ranges for the administration of the proteins of the present invention are those large enough to produce the desired immunotherapeutic effect, but not so large as to cause adverse side effects, such as unwanted cross-reactions, anaphylactic reactions, and the like. Generally, the dosage employed will vary with the age, condition, sex, and extent of the disease in the patient. Contraindications (if any), immune tolerance and other variables also will affect the proper dosage. Administration may be parenteral, by injection or by gradual perfusion over time. Administration also may be intravenous, intraperitoneal, intrarnuscular, subcutaneous, or intradermal.

Preparations for parenteral administration include sterile or aqueous or non-aqueous solutions, suspensions and emulsions. Examples of non-aqueous solvents include propylene glycol, polyethylene glycol, vegetable oils such as olive oil, and injectable organic esters such as ethyl oleate. Aqueous carriers include water, alcoholic and aqueous solutions, emulsions, or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives also may be present, such as, for example, antimicrobials, antioxidants, chelating agents, inert gases and the like. Such preparations, and the manner and method of making them, are known and described, for example, in Remington's Pharmaceutical Science, 16th ed., supra.

The proteins of the present invention also may be prepared as medicaments or pharmaceutical compositions comprising the proteins, either alone or in combination with other proteins or other agents such as lymphokines, monokines, and drugs, the medicaments being used for therapy of animal, including human, immune-related indications.

Although the proteins of the present invention may be administered alone, it is preferred that they be administered as a pharmaceutical composition. The compositions of the present invention comprise at least one protein or its pharmaceutically acceptable salt, together with one or more acceptable carriers and optionally other therapeutic agents. By "acceptable" is meant that the agent or carrier be compatible with other ingredients of the composition and not injurious to the patient. Compositions include those suitable for oral, rectal, nasal, topical (including buccal and sublingual), vaginal, or parenteral administration. The compositions conveniently may be presented in unit dosage form, and may be prepared by methods well known in the pharmaceutical arts. Such methods include bringing into association the active ingredient with the carrier that constitutes one or more accessory ingredients. In general, compositions are prepared by uniformly and intimately bringing into association the active ingredient with liquid carriers or finely divided solid carriers, or both, and shaping the product formed thereby, if required.

Orally administered pharmaceutical compositions according to the present invention may be in any convenient form, including capsules, cachets, or tablets, each containing a predetermined amount of the active ingredient. Powders or granules also are possible, as well as solution or suspension in aqueous or nonaqueous liquids, or oil-in-water liquid emulsions, or water-in-oil liquid emulsions. The active ingredient also may be presented as a bolus, electuary or paste.

Another embodiment of the present invention includes a method to regulate a cellular function selected from the group consisting of immunoglobulin heavy chain class switching, cytokine production or inflammatory cell activation, comprising regulating the activity of a CD154 protein. Regulation of activity of such protein can be achieved by sequestering CD154 protein in an inactive complex, regulating the ligand binding activity of CD154, and combinations thereof.

Suitable compounds for sequestering a CD154 protein in an inactive complex, include compounds that mimic the site at which CD154 protein interacts with CD40. Suitable compounds for regulating the binding activity of CD154 include CD40 antagonists of extracellular ligands to CD154.

Suitable methods for regulating the expression of endogenous and/or heterologous nucleic acid molecules encoding CD154 protein include methods known to those in the art. For example, oligonucleotides for use in, for example, antisense-, triplex formation-, ribozyme- and/or RNA drug-based technologies can be used to reduce expression of endogenous nucleic acid molecules encoding CD154 protein. The present invention, therefore, includes such oligonucleotides and methods to interfere with the production of CD154 protein by use of one or more of such technologies. Appropriate expression vectors can be developed by those skilled in the art based upon the cell-type being transformed.

In accordance with the present invention, a "mimetope" refers to any compound that is able to mimic the ability of a regulatory reagent of the present invention. A mimetope can be a peptide that has been modified to decrease its susceptibility to degradation but that still retains regulatory activity. Other examples of mimetopes include, but are not limited to, protein-based compounds, carbohydrate-based compounds, lipid-based compounds, nucleic acid-based compounds, natural organic compounds, synthetically derived organic compounds, anti-idiotypic antibodies and/or catalytic antibodies, or fragments thereof having desired regulatory activity. A mimetope can be obtained by, for example, screening libraries of natural and synthetic compounds for compounds capable of altering the activity of CD154, as disclosed herein. A mimetope can also be obtained by, for example, rational drug design. In a rational drug design procedure, the three-dimensional structure of a compound of the present invention can be analyzed by, for example, nuclear magnetic resonance (NMR) or x-ray crystallography. The three-dimensional structure can then be used to predict structures of potential mimetopes by, for example, computer modeling. The predicted mimetope structures can then be produced by, for example, chemical synthesis, recombinant DNA technology, or by isolating a mimetope from a natural source (e.g. plants, animals, bacteria and fungi).

Another embodiment of the present invention comprises administering to an animal, a therapeutic composition capable of regulating a biological function including immunoglobulin heavy chain class switching, cytokine production or inflammatory cell activation. A therapeutic composition of the present invention is particularly useful for preventing or treating diseases involving undesired immunoglobulin and/or cytokine production, or inflammatory cell activation. In particular, a therapeutic composition is useful for preventing or treating diseases involving an allergic or autoimmune response. Preferably, a therapeutic composition of the present invention is used to prevent or treat a disease, including, but not limited to, allergic hypersensitivity, asthma, rheumatoid arthritis, systemic lupus erythematosus (SLE), allergic rhinitis, atopic dermatitis and acute bronchopulmonary aspergillosis. A therapeutic composition is preferably administered to a cell having CD40 and more preferably to cells including, but not limited to, Pre-B cells, B lymphocytes, cancer cells, fibroblasts, Langerhans cells, epithelial cells monocytes and dendritic cells.

A variety of therapeutic compositions can be used to perform the regulation method of the present invention. Such therapeutic compositions include those compounds described in detail herein, in particular, compounds identified using a method of the present invention. A therapeutic composition of the present invention can be formulated in an excipient that the animal to be treated can tolerate. Examples of such excipients include those described in detail above. In order to regulate heavy chain class switching in a cell, a therapeutic composition of the present invention can be administered in vivo (i.e., in an animal) or ex vivo (i.e., outside of an animal, such as in tissue culture), in an effective manner such that the composition is capable of regulating heavy chain class switching.

An effective administration protocol (i.e., administering a therapeutic composition in an effective manner) comprises suitable dose parameters and modes of administration that result in prevention or treatment of a disease. Effective dose parameters and modes of administration can be determined using methods standard in the art for a particular disease. Such methods include, for example, determination of survival rates, side effects (i.e., toxicity) and progression or regression of disease. For example, the effectiveness of dose parameters and modes of administration of a therapeutic composition of the present invention can be determined by assessing response rates. Such response rates refer to the percentage of treated patients in a population of patients that respond with either partial or complete remission.

In accordance with the present invention, a suitable single dose size is a dose that is capable of preventing or treating an animal with a disease when administered one or more times over a suitable time period. Doses can vary depending upon the disease being treated. For example, in the treatment of hypersensitivity, a suitable single dose can be dependent upon the nature of the immunogen causing the hypersensitivity.

It will be apparent to a person of skill in the art that the number of doses administered to an animal is dependent upon the extent of the disease and the response of an individual patient to the treatment. For example, in the case of allergic responses, the immunogenicity of a compound may require more doses than a less immunogenic compound. Thus, it is within the scope of the present invention that a suitable number of doses, as well as the time periods between administrations, include any number required to treat a disease.

Therapeutic compositions can be administered directly to a cell in vivo or ex vivo or systemically. Preferred methods of systemic administration, include intravenous injection, aerosol, oral and percutaneous (topical) delivery. Intravenous injections can be performed using methods standard in the art. Aerosol delivery can also be performed using methods standard in the art (see, e.g., Stribling et al., Proc. Natl. Acad. Sci. (USA),189:11277-11281, (1992)), which is incorporated herein by reference in its entirety). Oral delivery can be performed by complexing a therapeutic composition of the present invention to a carrier capable of withstanding degradation by digestive enzymes in the gut of an animal. Examples of such carriers, include plastic capsules or tablets, such as those known in the art. Topical delivery can be performed by mixing a therapeutic composition of the present invention with a lipophilic reagent (e.g., DMSO) that is capable of passing into the skin.

Another embodiment of the present invention includes methods for treating platelets with an agent that modulates or inhibits sCD154 release, such as a metalloproteinase inhibitor, in order to prevent or treat inflammation in patients receiving transfusion of platelets. Platelets can be treated with CD154 inhibitors at various stages from during storage through the post-transfusion period. Treatment of platelets can also be done in any combination of the various stages.

As used herein, CD40L or sCD40L is interchangeable with CD154 or sCD154L. As used herein, "CD154 inhibitor" includes any compound that inhibits or reduces the production, secretion, release, binding, uptake or biological activity of CD154 or sCD154 in vivo, ex vivo, or in vitro. A CD154 inhibitor may also be an agent that performs, enhances, promotes or accelerates the degradation, decay or destruction of CD154 or sCD154. Preferably, a CD154 inhibitor will inhibit or reduce the production, secretion, release, binding, uptake or biological activity of CD154 or sCD154 by at least about 10% or 20%, more preferably by at least about 30% or 40%, still more preferably by at least about 50% or 60%, yet more preferably by at least about 70% or 80% and most preferably by at least about 90%.

As used herein, "metalloproteinase inhibitor" includes any compound which inhibits the enzymes involved in the hydrolysis of CD154 upon platelet stimulation, inhibits the metalloproteases' activities, or inhibits the cleavage of CD154 via a metalloprotease dependent mechanism. Examples of metalloproteinase inhibitors include the compound TAPI ($HONHCOCH_2CH(CH_2CH(CH_3)_2$—CO—$NaI$-Ala-$NHCH_2CH_2NH_2$), commercially available from Peptides International, Louisville, Ky., which blocks the hydrolysis of CD154; Galardin, N-[(2R)-2-(Hydroxamidocarbonylmethyl)-4-methylpentanoyl]-L-tryptophan methylamide), GM6001, available from Calbiochem, La Jolla, Calif.; doxycycline, -6-Deoxy-5-hydroxytetracycline; and SB-3CT(MMP-2/MMP-9 inhibitor VI), all commercially available from Calbiochem. Other macromolecular metalloproteases that can be purified from tissue or can be made as recombinant proteins include TIMP (tissue inhibitors of metalloproteases), commercially available from Calbiochem such as TIMP-1, TIMP-2, TIMP-3 or TIMP4. One of ordinary skill in the art would readily understand that the term "metalloproteinase inhibitor" would include any compound which shares the biological property of TAPI to block the hydrolysis of CD154. Further examples of metalloproteinase inhibitors include (3S)-(−)-[2-(4-Methoxybenzenesulfonyl)-1,2,3,4-tetrahydroisoquinoline-3-hydroxamate], N-Isobutyl-N-(4-methoxyphenylsulfonyl)-glycylhydroxamic Acid, N-Hydroxy-1-(4-methoxyphenyl)sulfonyl-4-benzyloxycarbonylpiperazine-2-carboxamide, N-Hydroxy-1-(4-methoxyphenyl)sulfonyl-4-(4-biphenylcarbonyl) piperazine-2-carboxamide, N-Hydroxy-1,3-di-(4-methoxybenzenesulphonyl)-5,5-dimethyl-[1,3]-piperazine-2-carboxamide, N-[(2R)-2-(Hydroxamidocarbonylmethyl)-4-methylpentanoyl]-L-tryptophan Methylamide, N-[[(4,5-Dihydro-5-thioxo-1,3,4-thiadiazol-2-yl)amino]carbonyl]-L-phenylalanine Methyl Ester, N-[[(4,5-Dihydro-5-thioxo-1,3,4-thiadiazol-2-yl)amino]carbonyl]-L-phenylalanine, (2R)-[(4-Biphenylylsulfonyl)amino]-N-hydroxy-3-phenylpropionamide, (3R)-(+)-[2-(4-Methoxybenzenesulfonyl)-1,2,3,4-tetrahydroisoquinoline-3-hydroxamate], α-[[[(4,5-Dihydro-5-thioxo-1,3,4-thiadiazol-2-yl)amino]carbonyl]amino]-N-(cyclohexylmethyl)-(S)-benzenepropanamide, α-[[[4,5-Dihydro-5-thioxo-1,3,4-thiadiazol-2-yl)amino]carbonyl]amino]-((2-pyridyl)piperazinyl)-(S)-benzenepropanamide, α-6-Deoxy-5-hydroxytetracycline, 7-Aza-2-phenylbenzisothizol-3-one, 7-Dimethylamino-6-demethyl-6-deoxytetracycline, HCl, (2R)-2-[(4-Biphenylylsulfonyl)amino]-3-phenylpropionic Acid, N-t-Butoxycarbonyl-L-leucyl-L-tryptophan Methylamide, N-[(2R)-2-(Carboxymethyl)-4-methylpentanoyl]-L-tryptophan-(S)-methyl-benzylamide, Chlorhexidine, Dihydrochloride, 1,6-bis[N-(p-Chlorophenyl)-N$^5$-biguanido]hexane, 2HCl, CHX, CL-82198, XG076, Vibramycin, HCl, (±)-(3R,5S,6E)-7-[3-(4-Fluorophenyl)-1-isopropylindol-2-yl]-3,5-dihydroxy-6-heptenoate, Doxycycline, Hydrochloride, Fluvastatin, FN-439, GM1489, GM6001, MMP Inhibitor I, MMP Inhibitor II, MMP Inhibitor III, M Inhibitor IV, MMP Inhibitor Set I, MMP-2 Inhibitor I, MMP-2/MMP-3 Inhibitor I, MMP-2/MMP-3 Inhibitor II, MMP-2/-3 Inhibitor III, MMP-2/MMP-3 hibitor IV, MMP-3 Inhibitor I, MMP-3 Inhibitor II, MMP-3 Inhibitor III, MMP-3 Inhibitor IV, MMP-3 Inhibitor V, MMP-3 Inhibitor VI, MMP-8 Inhibitor I, MMP-9/MMP-13 Inhibitor I, MMP-9/MMP-13 Inhibitor II, NNGH, OA-Hy, cis-9-Octadecanoyl-N-hydroxylamide, Oleolyl-N-hydroxylamide, Ac-RCGVPD-NH2, SB-3CT, stromelysin-1 Inhibitor, Vibramycin HCl, XG076, CL-82198 and HONH—COCH$_2$CH$_2$—FA-NH$_2$. Preferred metalloproteinase inhibitors include TAPI-1, Galardin, doxycycline or SB-3CT (MMP-2/MMP-9 inhibitor VI, more preferably, TAPI-1 or Galardin. Most preferably, the metalloproteinase inhibitor used in the method of the present invention would be one suitable for in vivo use in a patient such as Galardin. For macromolecular metalloproteases, preferred inhibitors include TIMPs, more preferably, TIMP-1, TIMP-2, TIMP-3 or TIMP-4, most preferably, TIMP-2.

As used herein, "container" means any vessel in which whole blood, megakaryocytes, platelets, CD154 inhibitors or metalloproteinase inhibitors may be kept for any period of time outside the body of the recipient or donor. This would include: cell culture dishes and/or flasks; syringes; blood collection and/or separation bags, tubes, needles and/or apparatus; platelet storage bags, test tubes and tubing. This listing of containers is merely exemplary in nature and is non-limiting in regard to the types of containers that may be used in the practice of the preset invention.

When platelets are incubated in the presence of a metalloproteinase inhibitor during storage, the metalloproteinase inhibitor can either be added to the storage container prior to addition of the platelets, for example, but not limited to, by coating the container with the metalloproteinase inhibitor or by sterile injection of the metalloproteinase inhibitor into the container. Alternatively, the metalloproteinase inhibitor can be added to the storage container after the platelets have already been collected therein, either prior to the start of or anytime during the storage procedure. The platelets being incubated with metalloproteinase inhibitor can then be stored in the same manner(s) already conventional in the art. Preferably, the metalloproteinase inhibitor is present in the storage container with the platelets at a concentration of or about 0.5 ng/ml through to or about 10 mg/ml. More preferably, the metalloproteinase inhibitor is present in the storage container with the platelets at a concentration of or about 5 ng/ml through to or about 1 mg/ml. Most preferably, the metalloproteinase inhibitor is present in the storage container with the platelets at a concentration of or about 50 ng/ml through to or about 05 mg/ml.

When platelets are treated with a metalloproteinase inhibitor following storage, but prior to administration to the transfusion recipient, the metalloproteinase inhibitor can either be added directly to the container which the platelets were stored in or to any container the platelets are in intermediate between the storage procedure and transfusion to the patient, up to and including the actual transfusion container. Preferably, the metalloproteinase inhibitor is added to the platelets after storage at a concentration of or about 0.5 ng/ml through to or about 10 mg/ml. More preferably, the metalloproteinase inhibitor is added to the platelets after storage at a concentration of or about 5 ng/ml through to or about 1 mg/ml. Most preferably, the metalloproteinase inhibitor is added to the platelets after storage at a concentration of or about 50 ng/ml through to or about 0.5 mg/ml.

When metalloproteinase inhibitor is to be administered directly to a patient in conjunction with said patient receiving a platelet transfusion, the metalloproteinase inhibitor can be administered to the patient before the platelets, concurrently with the platelets or subsequent to platelet transfusion. Additionally, the metalloproteinase inhibitor can be locally or systemically administered to the patient at either the same site as the platelets are administered or at a different site, or in any combination of these factors. When a metalloproteinase inhibitor is to be administered to said patient concurrently with the administration of the platelets, the metalloproteinase inhibitor can be administered as part of the same composition as the platelets and/or as a separate composition with a pharmaceutically acceptable carrier.

The metalloproteinase inhibitor can be administered to the platelet transfusion recipient in a variety of manners. Such methods of administration include injection via an intravenous, subcutaneous, intramuscular or intradermal route, for example. The metalloproteinase inhibitor may also be administered via shaped or implanted articles or by transdermal patch. Other methods of delivery could include oronasal or enteric administration of the metalloproteinase inhibitor, for example. A preferable method of administration of metalloproteinase inhibitor can include a therapeutic profile having quick onset of the effective dose and a release formulation that permits steady release. This list is exemplary and non-exhaustive in nature, and should not be considered limiting upon the present invention in regard to the manner in which a metalloproteinase inhibitor may be administered to a platelet transfusion recipient.

When a metalloproteinase inhibitor is administered directly to a platelet transfusion recipient, the delivery dosage should be in the range of or about 1 ng metalloproteinase inhibitor/kg body weight through to or about 500 mg/kg. Preferably, the delivery dosage should be in the range of or about 100 ng metalloproteinase inhibitor/kg body weight through to or about 100 mg/kg. More preferably, the delivery dosage should be in the range of or about 10 μg metalloproteinase inhibitor/kg body weight through to or about 50 mg/kg.

Most preferably, the delivery dosage should be in the range of or about 100 μg metalloproteinase inhibitor/kg body weight through to or about 20 mg/kg.

The following examples are provided for the purposes of illustration and are not intended to limit the scope of the present invention.

EXAMPLES

Example 1

Release of sCD154 from Platelets Upon Aggregation

Platelet-rich plasma (PRP) was prepared from human donors by obtaining blood through a 19-gauge butterfly into PPACK anticoagulant (8.6 ml of 2.1 mM PPACK, Calbiochem, La Jolla, Calif.: final concentration 0.3 mM). Blood was aliquoted into 15 ml polypropylene tubes and centrifuged at 900 rpm for 20 minutes (160×g). The platelet rich plasma (PRP) was carefully removed and pooled in a new tube. Platelet counts were taken and recorded. Aliquots of PRP at 37° C. were then added to 1.5 ml microcentrifuge tubes containing various amounts of INTEGRILIN®. To initiate aggregation, 20 μM ADP or 5 μM TRAP6 was added and samples were rocked on a Nutator for 30 minutes at 37° C. The tubes were put on ice and immediately centrifuged at 15,000× g for 10 minutes at 4° C.

The platelet-poor plasma (PPP) supernatant was removed to new tubes and the levels of sCD154 in these samples were measured by ELISA. There was a time-dependent increase in sCD154 release when platelets were aggregated with either ADP or TRAP6. This release was blocked in a dose dependent manner when platelets were incubated with INTEGRILIN® prior to the addition of agonist.

Example 2

Cloning and Expression of Human rsCD154

A cDNA of human sCD154 was prepared by reverse transcribing polyA RNA isolated from Jurkat cells using a forward primer (CGAATTCCTCTTCCATGGAAAA-CAGCTTTGAAATG; SEQ ID NO: 1) and a reverse primer (GACTCTTCGAAGCTAGGATCCTAGGGTTA; SEQ ID NO: 2) for CD154. cDNA expressing human sCD154 (108 a.a.-261 a.a.) was cloned in pDUAL vector (Stratagene) at Eam11041 restriction site. The clone was sequenced and confirmed to have the desired sequence. The cDNA has an artificially inserted methionine start site and expressed as an 18-kDa protein under a CMV promoter. cDNAs of sCD154 are transformed into bacterial strain BL23(DE3)-RIL to obtain maximum expression. Conditions for growth and optimal expression were standardized. rsCD154 was purified by lysing the bacterial pellet by sonication subjecting the lysate to two rounds of ion-exchange chromatography and one round of gel filtration. Sequencing confirmed that the purified protein was indeed sCD154.

Example 3

Biological Function of Bacterially Expressed Human rsCD154

Inflammation in the present invention study was measured by the upregulation of tissue factor on cultured endothelial cells. Endothelial cells were the cells selected for study as this is the most abundant cell exposed to blood and is known to express CD154, the ligand for CD154 (Yellin, M J, J. Exp Med, 182: 1857(1995)). Tissue factor was selected as the marker for inflammation because this protein is known to be up-regulated in response to CD154 (Slupsky, J R, Thromb. Haemost., 80: 1008 (1998)), to localize with all developmental stages of atherosclerotic lesion development (Wilcox, J N, Proc. Nat. Acad. Sci. (USA), 86: 2839 (1989); Annex, B H, Circulation, 91: 619 (1995)) and to initiate thrombosis.

Human umbilical vein endothelial cells (HUVECS) purchased from Clonetics Inc. were cultured with M199 containing 20% FBS, 50 μg/ml endothelial mitogen (Biomedical technologies Inc.) 2 mM glutamine, 1 mM Sodium Pyruvate, 1× Non-essential amino acids, 100 U/ml of penicillin/streptomycin and 100 μg/ml heparin. HUVECS (passage 3-5) grown in 6 well dishes or 96 well tissue culture plates coated with 0.75% bovine skin gelatin (Sigma chemicals) were incubated without and with different concentrations (100 ng-10 μg/ml) of rsCD154 in the presence of TRAP-1 (monoclonal antibody against hCD154, BD Pharmingen) or MOPC-21 (mouse IgG, Sigma) for 4 hrs at 37° C. in Tyrode's-Hepes buffer (12 mM NaHCO3, 138 mM NaCl, 5.5 mM glucose, 2.9 mM KCl, 10 mM Hepes, 1 mM $CaCl_2$, 1 mM $MgCl_2$, pH 7.4). The release of the soluble CD154 hydrolytic product was linear up to 30 min. In data not shown, in addition to the measurements made of the amount of sCD154 released per platelet from TRAP-aggregated platelets, measurements were also made of the amount of sCD154 released per platelet from ADP-aggregated platelets in PPACK-anticoagulated plasma. While inhibition of platelet aggregation with a glycoprotein IIb-IIIa antagonist INTEGRILIN® (eptifibatide; Millennium Pharmaceuticals, Inc.) did not affect thrombin- or TRAP-induced surface expression of CD154 or the release of thrombospondin, this GP IIb-IIIa antagonist inhibited the release of soluble CD154 in platelets activated by ADP and in platelets activated by TRAP.

The supernatants were collected and the concentrations of MCP-1 determined by ELISA. Expression of tissue factor was determined by clotting assays performed with the HUVECS in the 96 well plates. The media from aggregated platelets was found to induce the expression of tissue factor in human umbilical vein endothelial cells and the soluble form of CD154 was found to account for some of this activity. The expression of ICAM-1 and E-Selectin was determined by FACS analysis (FACSort, Beckton Dickinson) following release of the HUVECS from the dishes. HUVECS, when exposed to 2 μg/ml rsCD154, secreted 3 fold more MCP-1 after 4 hrs and this increase was blocked by anti-CD154 antibody, but not by an isotype matched control antibody. As measured by clotting assay there was 50% reduction in clotting time, which was reversed in the presence of TRAP-1. Also, changes in the surface expression of CD154 were determined by FACS analysis, which indicated that there was increased expression of ICAM-1 and E-Selectin by 2 fold with 2 μg/ml of rsCD154, which was blocked by TRAP-1.

In this example, changes were determined in CD154 distribution and apparent molecular weight during aggregation of washed platelets with TRAP, a potent platelet agonist that stimulates platelets through the PAR1 thrombin receptor. As previously described, CD154 exists as a 33/31 kDa doublet in unstimulated platelets. However, platelet aggregation was found to induce the hydrolysis of CD154, converting the 33/31 kDa doublet found in unstimulated platelets to a soluble, 18 kDa product. This 18 kDa hydrolytic fragment was recovered in the supernatant following removal of the aggregated platelets by centrifugation. Inhibition of platelet aggregation by the inclusion of 5 µM of a platelet glycoprotein IIb-IIIa antagonist (INTEGRILIN®) prevented CD154 hydrolysis, and the appearance of the soluble 18 kDa hydrolytic fragment. This inhibition of CD154 release occurred without affecting the TRAP-induced release of thrombospondin (data not shown). Similar data were obtained when the platelets were stimulated with thrombin. As was previously shown, platelet stimulation caused a marked enhancement of the surface expression of CD154. This enhancement was unaffected by the inclusion of INTEGRILM®.

These results indicate the bacterially expressed rsCD154 is biologically active. The activity was blocked by TRAP-1 (previously demonstrated as a blocking antibody). The results of these experiments show that platelet aggregation releases a cleaved, soluble form of CD154 that is capable of producing an inflammatory response in vascular endothelial cells. GP IIb-IIIa antagonism had the unexpected benefit of inhibiting the release of soluble CD154, a potent soluble proinflammatory mediator, even when platelets are activated by potent agonists.

Example 4

Validation of an ELISA Method for the Determination of sCD154 in Human Serum, EDTA Plasma and Citrate Plasma A sCD154 enzyme-linked immunosorbent assay (ELISA) used for the quantitative detection ofsCD154 in human serum, EDTA plasma and citrate plasma The sCD154 samples are incubated in an ELISA plate with anti-sCD154 monoclonal antibody coated wells to capture the free sCD154, and HRP-conjugated monoclonal anti-sCD154 antibody is employed to detect the presence of the captured sCD154. The detection of bound HRP-conjugate is achieved by adding tetramethylbenzidine (substrate) and peroxide and by measuring the absorbance at 450 nm.

The lower limit of quantitation for the human sCD154 ELISA is 0.156 ng/ml. The serum method has an inter-assay accuracy range of 85.0 to 93.3% and an inter-assay precision of 7.78 to 10.5% RSD of nominal value for QC samples (1.00 to 9.00 ng/ml). The EDTA plasma method has an inter-assay accuracy range of 97.1 to 115.0% and an inter-assay precision of 7.34 to 12.5% RSD of nominal value for QC samples. The citrate plasma method has an inter-assay accuracy range of 86.3 to 104.8% and an inter-assay precision of 6.15 to 21.4% RSD of nominal value for QC samples. The assay is linear over the analytical range of 0.156 to 10.0 ng/ml.

This sCD154 ELISA method has been applied to study sCD154 with patients undergoing glycoprotein IIb-IIIa inhibitor therapy. The method has been proven to be robust in the analysis of clinical samples in all three human matrices and will be used in other trials to study the function of these glycoprotein IIb-IIIa inhibitors on platelet aggregation and the role of sCD154 in coronary disease.

Example 5

Arterial Thrombus Formation in Mice Lacking CD154

The role of CD154 in thrombus formation was investigated using a model that compares wild type (WT) mice with CD154-/- mice that have impaired thrombosis. In this model, it was found that the time required for formation of the first thrombus diameter>20 µm is not significantly increased in the CD154-/- compared to WT mice, but surprisingly, the time for occlusion is significantly increased. It was observed that the occlusion time is approximately twice as long in the CD154-/- mouse as in wild type, apart from any other treatment effect.

In this example, the recombinant form of the soluble CD154 was infused into the CD154-/- mouse. Thrombus formation was evaluated using the model as described below.

To perform the investigation, the intravital microscopy thrombosis model of the mouse mesentery was used (Denis et al., *PNAS*, 95:9524-9, (1998)). The interactions of fluorescently-labeled platelets with a FeCl$_3$-injured arteriolar vessel wall (shear rate ~1300 s$^{-1}$) were analyzed. The early single platelet-vessel wall interaction (between 3 and 5 minutes after vascular injury), the time required for formation of thrombus (diameter>20 µM), as well as the time required for occlusion of the vessels were studied.

Blood was harvested from the retro-orbital venous plexus by puncture and collected in 1-mL polypropylene tubes (Eppendorf; Marsh Biochemical Products, Rochester, N.Y.) containing 10% final volume of acid-citrate-dextrose, 38 mmol/L citric acid, 75 mmol/L trisodium citrate, and 100 mmol/L dextrose). Platelet-rich plasma was obtained by centrifugation at 220 g for 7 minutes. The plasma and the buffy coat were gently transferred to a fresh polypropylene tube containing 0.7 ml of a washing buffer (129 nmol/L NaCl; 13.6 mmol/L trisodium citrate; 11.1 mmol/L dextrose, 1.6 mmol/L KH2PO4, pH 6.8) in the presence of 1 µmol/L prostaglandin E1 (Sigma, St. Louis, Mo.), and centrifuged at 160 g for 4 minutes. The supernatant was transferred to 2 polypropylene tubes containing 3 ml of the washing buffer. After centrifugafion at 2000 g for 10 minutes, the pellet was re-suspended in resuspension buffer (137 mmol/L NaCl; 4 mmol/L KCl; 0.5 mmol/L MgCl$_2$; 0.5 mmol/L sodium phosphate; 11.1 mmol/L dextrose; 0.1% bovine serum albumin; 10 mmol/L HEPES, pH 7.4).

Platelets were fluorescently labeled with calcein AM 0.25 µg/ml (Molecular Probes, Eugene, Oreg.) for 15 minutes at room temperature. Fluorescent platelets (5×10$^9$ platelets/kg) were infused through the tail vein.

Immediately after infusion of fluorescent platelets into mice of matching genotypes (4- to 5-weeks old C57BL6J and CD15-/-), animals were anesthetized with 2.5% tribromoethanol (0.15 mL/10 g). An incision was made through the abdominal wall to expose the mesentery, and mesenteric arterioles of 60 to 100 µm diameter were studied. The shear rate (1000 to 1300 s$^{-1}$) was calculated using an optical Doppler velocimeter using known methods (see.e.g. *Blood.* November 2000). Arterioles were visualized using a Zeiss (Oberkochen, Germany) Axiovert 135 inverted microscope (objective 32×, 0.4 NA) equipped with a 100-W HBO fluorescent lamp source (Opti Quip, Highland Mills, NY) with a narrow-band fluorescein isothiocyanate filter set (Chroma Technology, Brattleboro, Vt.) and a silicon-intensified tube camera C2400 (Hamamatsu, Tokyo, Japan) connected to an SVHS video recorder (AG-6730; Panasonic, Tokyo, Japan).

Resting blood vessel was recorded for 2 minutes, then Ferric Chloride (30 µl of a 250-mM solution) was superfused, and video recording was resumed for another 40 minutes, or until full occlusion occurred and lasted for more than 10 seconds.

Time for appearance of the first thrombus bigger than 20 µm, time for occlusion of the blood vessel as well as the number of thrombi>30 µm that embolize before occlusion were analyzed.

FIGS. 1 and 2 present results of an experiment performed with the perfusion chamber showing a reduced mean thrombus height in CD40L-/- mice at 3200/s. These results do not show any differences in platelet aggregation induced by ADP, collagen or thrombin. The P-selectin redistribution on the surface of thrombin-activated platelets is the same, as well as on the surface of platelets adhering on a growing thrombus under circumstances of high shear (perfusion chamber, confocal microscopy). Data also shows a normal (total) phosphotyrosine profile in platelets (both WT and CD40L-/- mice) adhering to collagen under relatively high shear rates as observed using FITC 4G10 antibody on permeabilized thrombus in the perfusion chamber.

In this example, superfilsion of ferric chloride, platelets adhered transiently in both wild type (WT) and CD154-/- mice. The time to reach occlusion is significantly increased in CD154-/- mice, compared with WT, while there is no difference in the initiation of the thrombus, suggesting that the vWf-GPIbα interaction involved in the adhesion process and the subsequent platelet-platelet interactions are not affected by the lack of CD154. It may be more likely that, under circumstances of low shear stress, thrombus formation is normal in the CD40L-/- mice, but as the flow rate is increased, there is a deficiency in the CD40L-/- mice. This would explain the normal aggregation observed, because the normal aggregation was performed in an aggregometer, which is an environment of low shear stress.

Interestingly, we were able to reconstitute a normal thrombotic process in CD154-1-mice after injection of a single dose of human rsCD154 (26 µg/mouse), 5 to 10 minutes before the arteriole injury. We found that infusion of soluble CD154 eliminated the thrombosis defect in the CD154-/- mouse.

The increase in time to reach occlusion in CD154-/- mice is explained by an increased instability of the thrombus formed under high shear rate and exogenous addition of human rsCD154 stabilizes the thrombotic process, and is presently believed to act through a direct binding to platelets.

Example 6

Metalloproteinase Inhibitors Inhibit Platelet Aggregation and sCD154 Release

Washed platelets were prepared from blood drawn into $1/6^{th}$ volume of ACD containing (85 mM sodium citrate, 111 mM dextrose and 71 mM citric acid) with 0.05 µg/ml PGI2. Collected blood was centrifuged at 160×g for 20 minutes at room temperature (Beckman GP) and the PRP layer was collected. PRP was then centrifuged at 1100×g for 10 minutes to sediment platelets. Platelets were washed twice by resuspending in CGS (13 mM trisodium citrate, 120 mM NaCl, 30 mM Dextrose, pH 7.0) containing 0.05 µg/ml PGI2 for the first wash. The final suspension of platelets ($3\times10^8$/ml) was in Tyrode's Hepes.

a. For platelet aggregation studies, 500 µL of washed platelets were allowed to stir in a Chrono-Log Aggregometer before the addition of 1 µM TRAP6 to initiate aggregation. Subsequent samples included various metalloproteinase inhibitors added to washed platelets before the addition of TRAP6; 0.1-1.0 µg/ml TIMP-2 (Calbiochem) or 5-50 µM TAPI-1 (Peptides International). Aggregation proceeded for 5 minutes and the amplitude of each aggregometer tracing was calculated by Aggro-Link software.
  b. CD154 determinations were made as follows: Washed platelets were incubated at 37° C. with various concentrations of TIMP-2 and TAPI-1 (see above) while rocking on a Nutator for 30 minutes. Platelets or platelet aggregates were removed from suspension by centrifugation for 10 minutes at 15,000×g, 4° C. and the resulting supernatants were collected. The levels of sCD154 were measured by ELISA.

In these experiments, TIMP-2 and TAPI-1 inhibited platelet aggregation induced by sub-optimal concentrations of TRAP6 in a dose dependent manner. TIMP-2 and TAPI-1 inhibited the release of sCD154 from TRAP6-stimulated platelets.

Example 7

Metalloproteinase Inhibitors Inhibit sCD154 Release from the Activated Platelets Washed platelets were prepared from blood drawn into $1/6^{th}$ volume of ACD containing (85 mM sodium citrate, 111 mM dextrose and 71 mM citric acid) with 0.05 µg/ml PGI2. Collected blood was centrifuged at 160×g for 20 minutes at room temperature (Beckman GP) and the PRP layer was collected. PRP was then centrifuged at 1100×g for 10 minutes to sediment platelets. Platelets were washed twice by repeat suspending and pelleting in CGS (13 mM trisodium citrate, 120 mM NaCl, 30 mM Dextrose, pH 7.0) containing 0.05 µg/ml PGI2 for the first wash. The final suspension of platelets ($5\times10^8$/ml) was in Tyrode's Hepes.

The release of sCD40L from the activated platelets was determined as follows: 500 µL of washed platelets were gently mixed 5 µM of TRAP and incubated at 37° C. without rocking for 30 min. Under this condition, platelets were activated but not aggregated. 5-50 µM of metalloproteinase inhibitors GM6001 (Galardin, Calbiochem) or TAPI-1 (Peptides International) were added to the washed platelets before the addition of TRAP. Platelets were removed from suspension by centrifugation for 10 minutes at 15,000×g, 4° C. and the resulting supernatants were collected. The levels of sCD154 were measured by ELISA.

Figure 3:
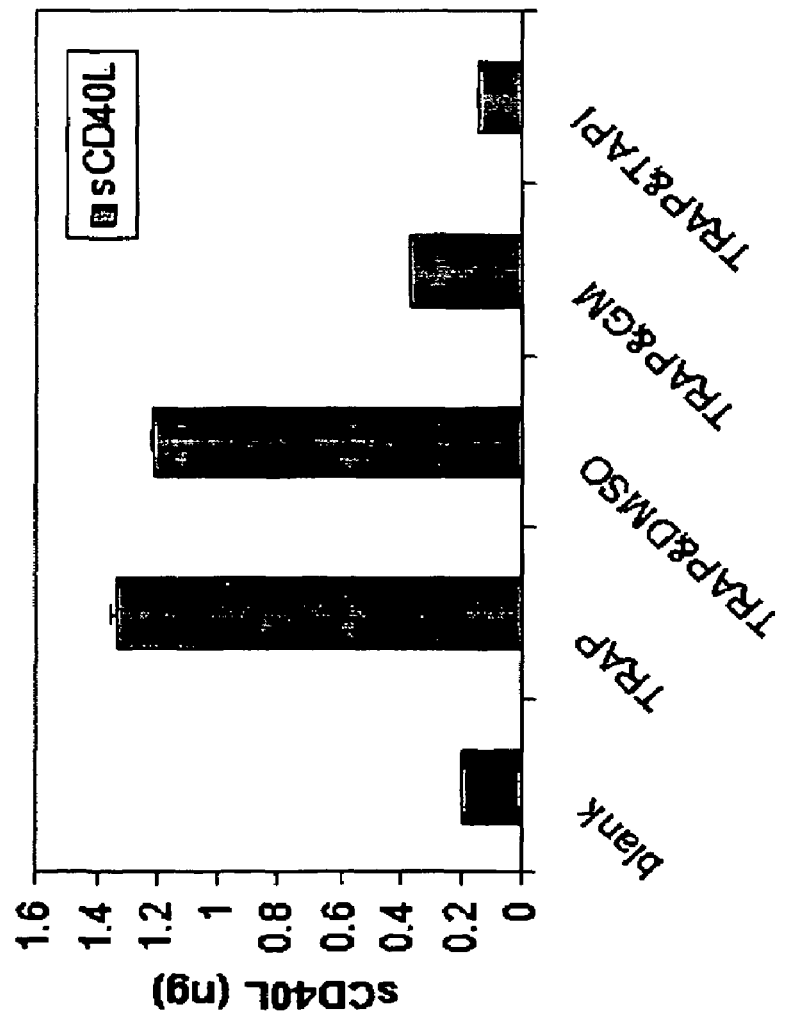
FIG. 3 shows the use of metalloproteinase inhibitor in decreasing sCD40L release.

In these experiments, GM6001 and TAPI-1 inhibited the release of sCD154 from TRAP-stimulated platelets in a dose-dependent manner. FIG. 3. shows that both 50 µM of GM6001 (GM) and TAPI-1 inhabited the release of sCD40L from TRAP activated, but not aggregated, platelets.

Example 8

Metalloproteinase Inhibitors Inhibit the Cleavage of CD40L into sCD40L in Platelets Washed platelets were prepared from blood drawn into $1/6^{th}$ volume of ACD containing (85 mM sodium citrate, 111 mM dextrose and 71 mM citric acid) with 0.05 µg/ml PGI2. Collected blood was centrifuged at 160×g for 20 minutes at room temperature (Beckman GP) and the PRP layer was collected. PRP was then centrifuged at 1100×g for 10 minutes to sediment platelets. Platelets were washed twice by repeat suspending and pelleting in CGS (13 mM trisodium citrate, 120 mM NaCl, 30 mM Dextrose, pH 7.0) containing 0.05 µg/ml PGI2 for the first wash. The final suspension of platelets ($5 \times 10^8$ /ml) was in Tyrode's Hepes.

The cleavage of CD40L into sCD40L was revealed with immunoblotting of different forms of CD40L in the platelet lysates. Cleavage of the full length CD40L (32 kD) yields the 18 kD soluble from (sCD40L). 500 µl of Washed platelets were gently mixed with TRAP (5 µM) to initiate the platelet activation. Metalloproteinase inhibitors GM6001 (50 µM, Calbiochem) or DMSO were added to washed platelets, and incubated at 37° C. with or without rocking for 30 minutes. Platelets aggregated when rocked in the presence of TRAP, but were activated but not aggregated without rocking. Platelets were removed from suspension by centrifugation for 10 minutes at 15,000×g, 4° C. and the resulting platelet pellets were dissolved in the loading buffer. The proteins in the platelet lysates were resolved with SDS-PAGE, transferred onto nitrocellulose membrane, and blotted with anti-CD40L antibody (MK13A4, Alexis).

Figure 4:
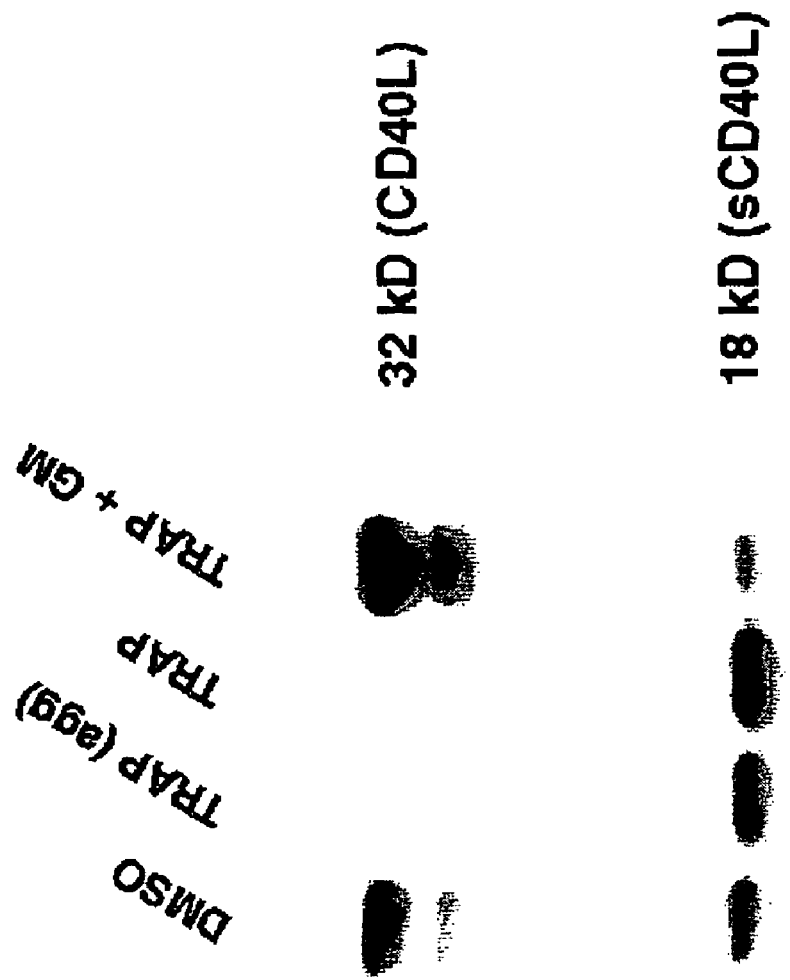
FIG. 4 shows CD40L cleavage by metalloproteinase.

FIG. 4 shows that in these experiments, TRAP induced the cleavage of CD40L to sCD40L both in the sample of activated platelets and in the platelets aggregation (agg). GM6001 (GM) inhibited the cleavage of the full length CD40L to the 18 kD soluble from. Same results were obtained with another metalloprotease inhibitor TAPI-1 (Peptide International, Inc.) A separated example showed that a control inactive compound GM1012 (Calbiochem) did not affect the cleavage. Therefore, the hydrolysis of CD40L was attributed to the function of metalloproteases in the platelets.

Example 9

Incubation of Stored Platelets with Metalloproteinase Inhibitor

Platelets are obtained and separated from whole peripheral blood of the patient or from allogeneic donors via apheresis. Platelets are stored at 20-24° C. under constant agitation in anti-coagulant-treated donor serum for a total volume of 50-70 ml in a collapsible container standard in the art. 9.7 mg of Galardin to a final 500 µmolar concentration is sterilely added through an injection port in the container. Platelets are allowed to incubate in the metalloproteinase inhibitor containing serum for up to the maximum time of at least 6 days recommended for platelet storage. Platelets are prepared for transfusion in the usual manner and transfused into the patient.

To monitor the effect of metalloproteinase inhibitor on CD40L release during the storage, 50-70 ml of concentrated platelets from single donor were divided into two equal portions and stored in two collapsible platelet bags. The metalloprotease inhibitor Galardin dissolved in DMSO was added to one bag, and the control DMSO was added into the other bag of platelets from the same donor. 2 ml of platelets was taken from each bag every day in following 5 days. The platelets were separated from the supernatant by centrifugation at 2000 rpm for 10 min. The supernatants were centrifuged again at 15,000 rpm for 10 min in a desktop centrifuge to yield the plasma samples. The platelet pellets were dissolved in a lysis buffer. The CD40L levels in both plasma and platelet samples were determined with ELISA.

Figure 5:
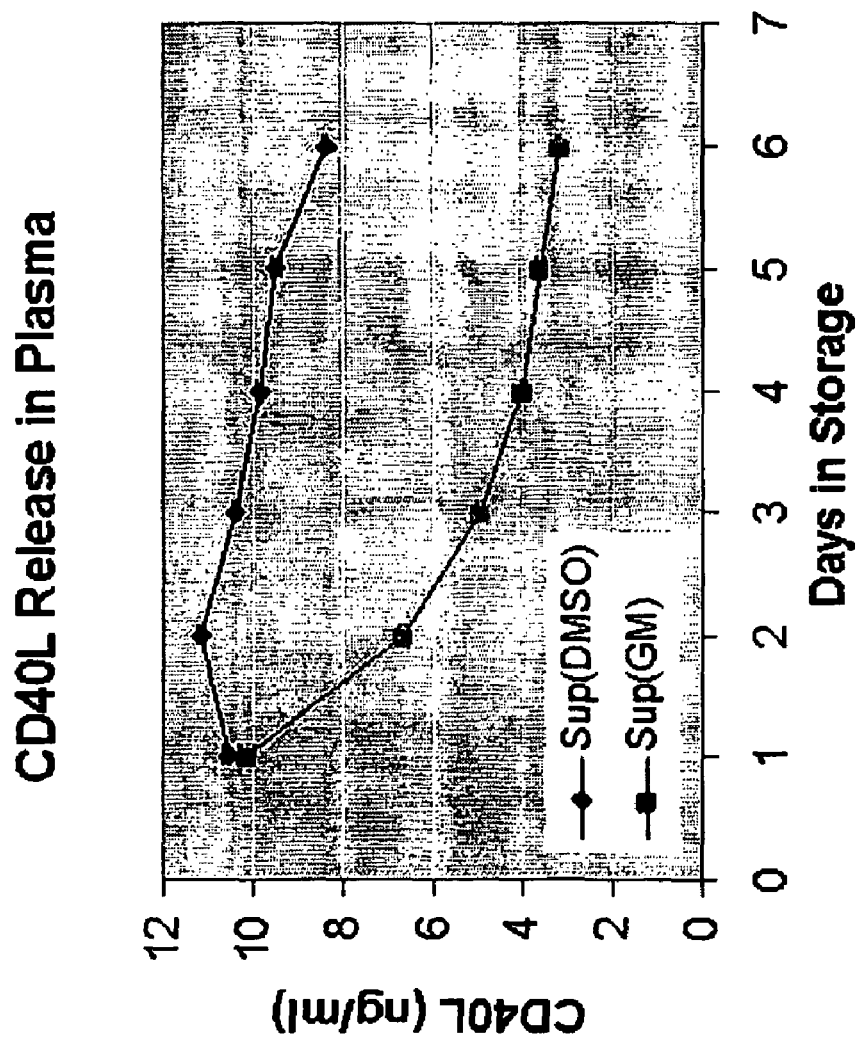
FIG. 5 shows a comparison of CD40L release in plasma after 6 days storage.
Figure 6:
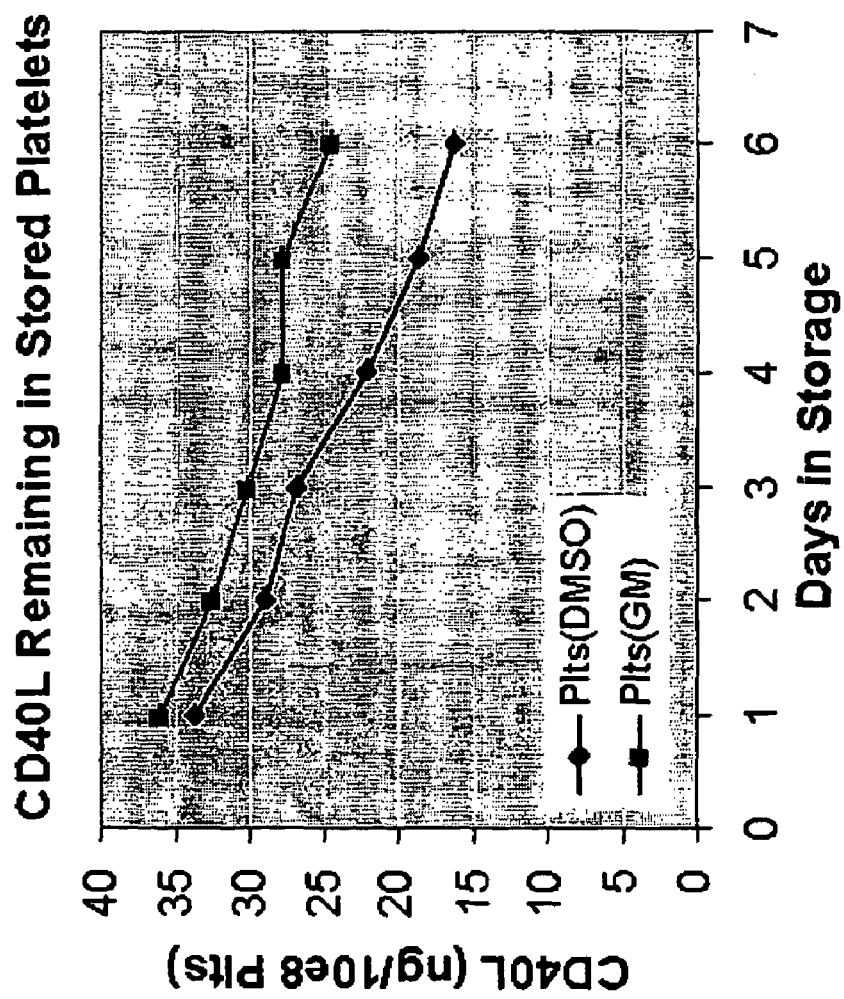
FIG. 6 shows a comparison of CD40L release in platelets after 6 days storage.

FIG. 5 shows that metalloproteinase inhibitors reduced the release of CD40L into plasma from stored platelet concentrates. Concurrently, there were higher CD40L levels remaining in the platelets during the storage in the presence of metalloprotease inhibitor (FIG. 6).

Example 10

Treatment of Stored Platelets with Metalloproteinase Inhibitor

Platelets from the patient or from allogeneic donors, which have been stored by standard methods, are prepared for transfusion in the usual manner. During preparation for transfusion, about 9.7 mg to about 12 mg of Galardin to a final 500 µmolar concentration is sterilely added to the platelet composition. The metalloproteinase inhibitor treated platelets are transfused into the patient in the usual manner.

Example 11

Treatment of Platelet Transfusion Recipients with Metalloproteinase Inhibitor

Platelets from the patient or from allogeneic donors, which have been stored by standard methods, are transfused into the patient in the usual manner. During transfusion, Galardin is sterilely injected into the transfusion apparatus through an injection port for a final concentration of about 10 mg/kg patient body weight. In some patients, the repeated administration of about 10 mg Galardin/kg patient body weight, at least three times a day for a period of about 10 to about 14 days is desirable.

Example 12

Effect of CD154 on Platelet Aggregation Under High Shear Stress

The effect of CD154 on the aggregation of platelets under conditions of high shear stress were evaluated. Recombinant CD154 (rCD154 or rCD40L) was compared to fibrinogen (Fg) in its ability to form thrombi as well as in combination with Fg. Controls also included CD154 in which the KGD INTEGRILIN®-recognition sequence was mutated to KGE (CD154(KGE) or CD40L(KGE)). Briefly, a silicone gasket with a flow path height of 127 µm was placed between a flat perfusion chamber (Glycotech, Rockville, Md.) and a protein-coated petri dish as described (André, P. et al., Nature Medicine, 8:247-252 (2002)). Petri dishes were coated with rCD40L, Fibrinogen (Fg), rCD40L+Fg, mutated CD40L (CD40L(KGE)), CD40L(KGE)+Fg. In one experiment, the glycoprotein IIb/IIIa antagonist INTEGRILIN® (2 µM) was incubated with whole blood before perfilsion over the rCD40L-coated surface. When Fg was coated with either rCD40L or CD40L(KGE), each molecule was deposited at 25 µg/cm². Coating of the proteins was performed using the spray method in which 25 µl of a 1 mg/ml protein solution is coated onto the plastic with a retouching air brush resulting in a concentration of 25 µg/cm² (Houdijk, W P et al., J. Clin. Invest., 75:531-540 (1985)). Human peripheral blood was collected on PPACK (40 µmol/L final concentration) and perfused for 4 minutes over the protein-coated surface. Shear rates of 1500-1600/s, 500-600/s and 100-200/ s, were generated with flow rates of 0.6, 0.25 and 0.075 ml/min, respectively. Measurements of thrombotic deposits were performed using the Simple PCI software image analysis program (Technical Instrument, Burlingame, Calif.).

Figure 7:
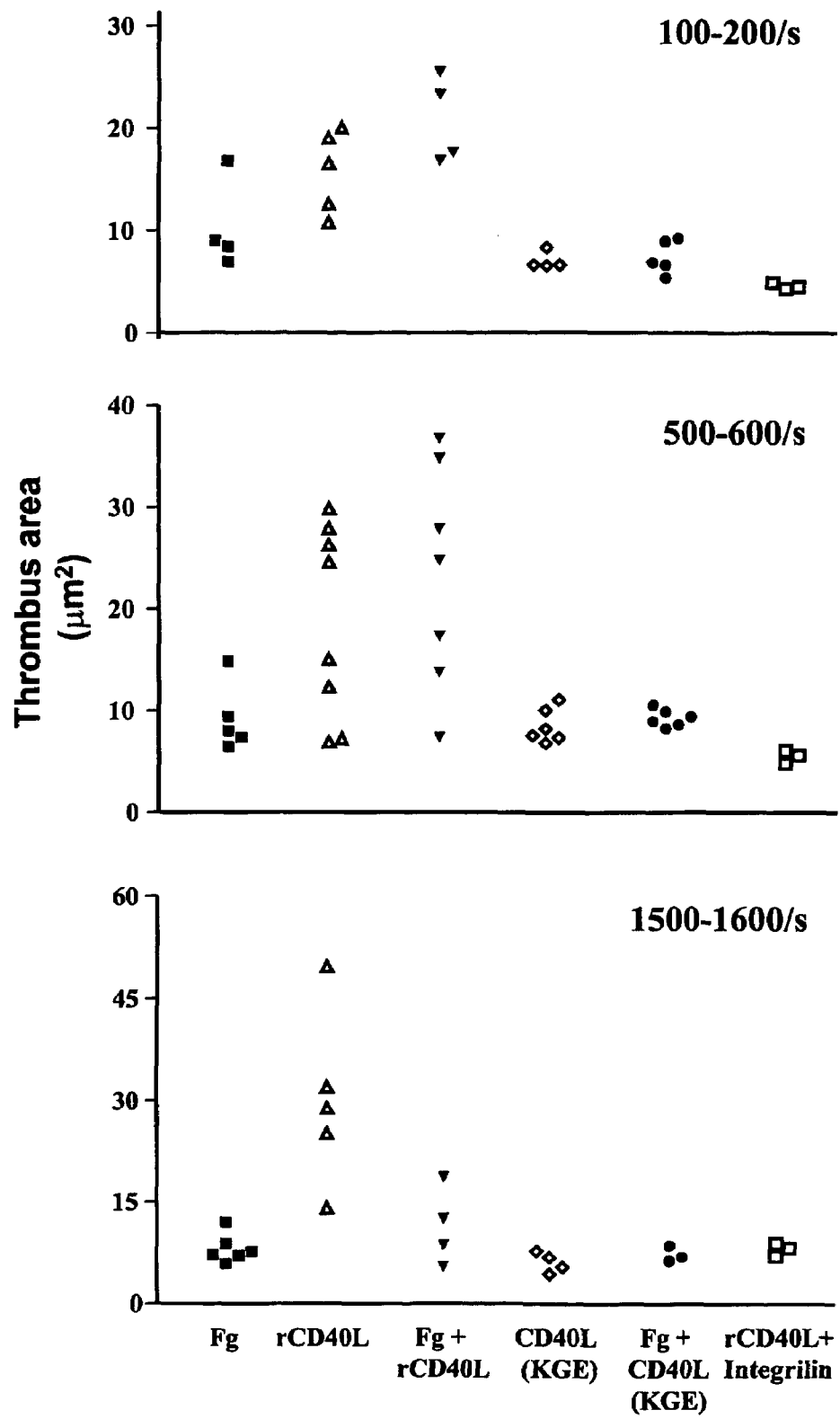
FIG. 7 shows the raw data of the mean thrombus area per experiment for the three different shear rates.
Figure 8:
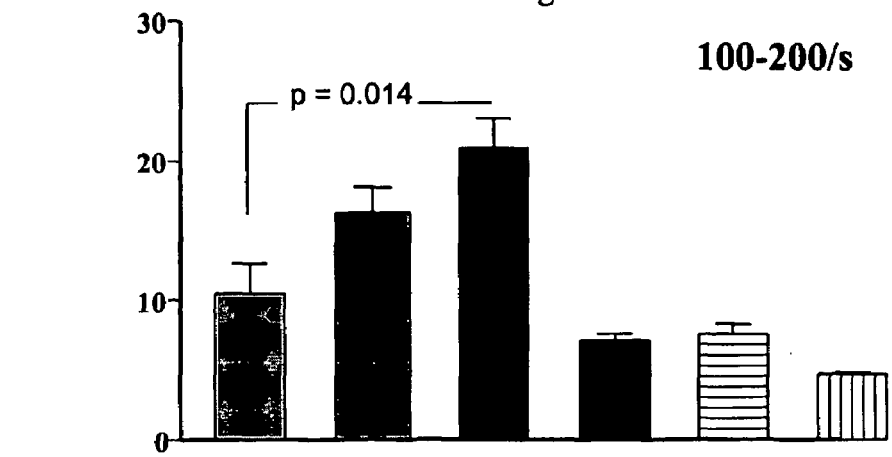
FIG. 8 shows the mean thrombus area per group and per shear rate.
Figure 8:
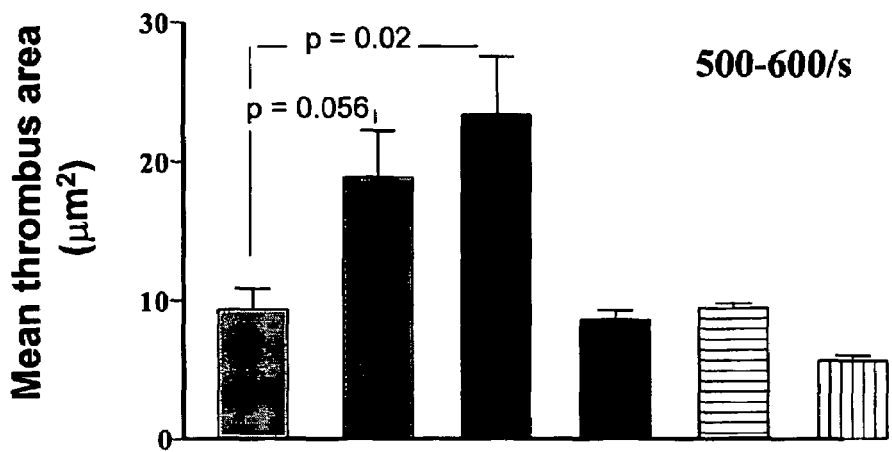
Figure 8:
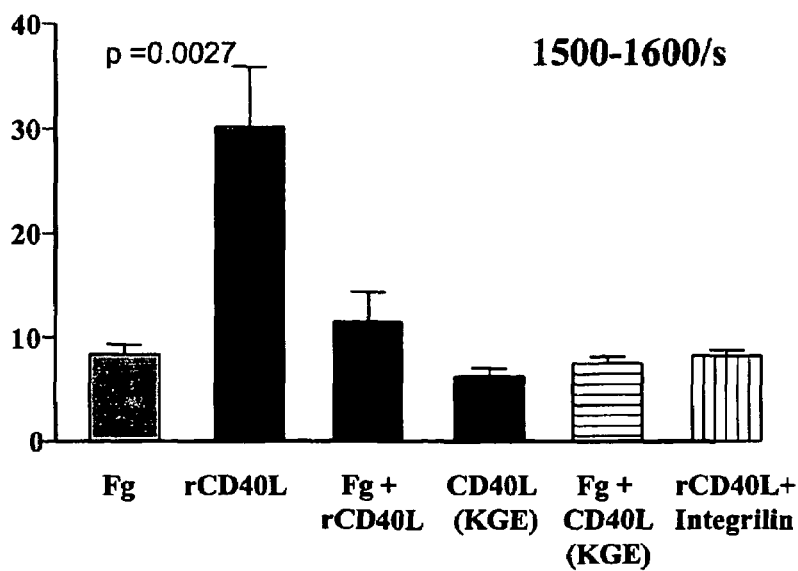
Figure 9:
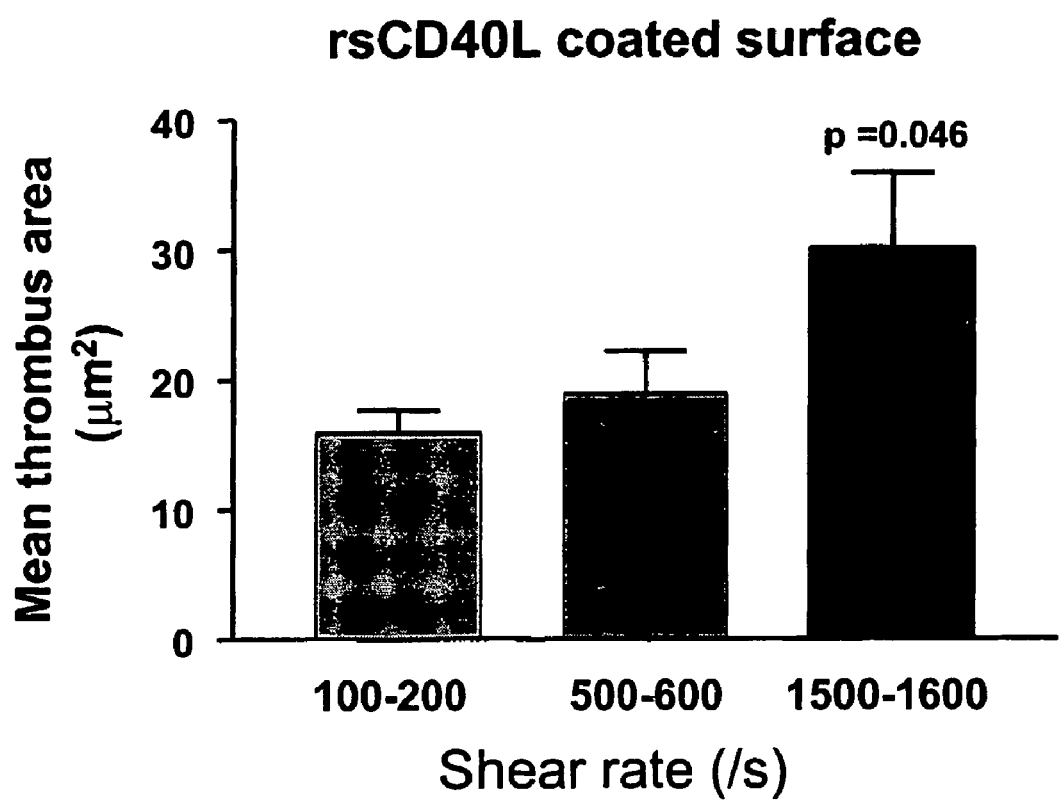
FIG. 9 shows the mean thrombus area on the rCD40L coated surface versus shear rate.

FIG. 7 represents the raw data of the mean thrombus area per experiment for the three different shear rates. FIG. 8 represents the mean thrombus area per group and per shear rate. Statistical analysis (Student's t test) and graphs were performed using the GraphPad PRISM program (GraphPad Software, Inc., San Diego, Calif.). Mean thrombus area is increased at shear rates of 100-200/s and 500-600/s when rCD40L and Fg are coated together, but this increase disappears at 1500-1600/sec, perhaps due to embolization of the Fg. However, at a shear rate of 1500-1600/s, rCD40L alone significantly enhances the aggregation process versus Fg. CD40L(KGE) does not induce aggregate formation either in the absence or absence of Fg. Binding of platelets to the rCD40L is inhibited by INTEGRILIN®. FIG. 9 represents the mean thrombus area on the rCD40L coated surface versus shear rate showing a shear-dependent significant increase of the mean thrombus area.

Although the present invention has been described in detail with reference to examples above, it is understood that various modifications can be made without departing from the spirit of the invention. All cited patents, patent applications and publications referred to in this application are herein incorporated by reference in their entirety.

We claim:

1. A method for the treatment of thrombosis in a subject comprising the administration of a CD154 inhibitor in an amount effective to inhibit the release of soluble CD154 (sCD154) from a platelet.

2. The method of claim 1, wherein the release of soluble CD154 from a platelet is inhibited by at least about a % amount selected from the group consisting of 90%, 80%, 70%, 60%, 50%, 40%, 30%, 20% and 10%.

3. The method of claim 2, wherein said CD154 inhibitor is a metalloproteinase inhibitor.

4. The method of claim 3, wherein the metalloproteinase inhibitor is selected from the group consisting of $HONHCOCH_2CH(CH_2CH(CH_3)_2$—CO—NaI-Ala-$NHCH_2CH_2NH_2$(TAPI-1), tissue inhibitor of metalloprotease-2 (TIMP-2), doxycycline, galardin and SB-3CT (MMP2/MMP9 inhibitor VI).

5. The method of claim 1, wherein the subject is further treated with at least one additional agent which blocks platelet aggregation or which enhances thrombolysis.

6. The method of claim 5, wherein said at least one additional agent which blocks platelet aggregation is a platelet glycoprotein GP IIb-IIIa antagonist.

7. The method of claim 6, wherein said GP IIb-IIIa antagonist is eptifibatide.

8. A method for the treatment of an inflammatory disorder associated with platelet transfusion in a platelet transfusion recipient comprising treating said platelets with a CD154 inhibitor in an amount effective to inhibit the release of soluble CD154 from said platelets.

9. The method of claim 8, wherein the platelets are treated with said CD154 inhibitor in vitro or ex vivo, prior to administration to said recipient.

10. The method of claim 8, wherein the platelets are treated with said CD154 inhibitor in vivo, after administration to said recipient.

11. The method of claim 8, wherein the release of soluble CD154 from a platelet is inhibited by at least about a % amount selected from the group consisting of 90%, 80%, 70%, 60%, 50%, 40%, 30%, 20% and 10%.

12. The method of claim 8, wherein said CD154 inhibitor is a metalloproteinase inhibitor.

13. The method of claim 12, wherein the metalloproteinase inhibitor is selected from the group consisting of $HONHCOCH_2CH(CH_2CH(CH_3)_2$—CO—NaI-Ala-$NHCH_2CH_2NH_2$(TAPI-1), tissue inhibitor of metalloprotease-2 (TIMP-2), doxycycline, galardin and SB-3CT (MMP2/MMP9 inhibitor VI).

14. The method of claim 8, wherein the subject is further treated with at least one additional agent which blocks platelet aggregation or which enhances thrombolysis.

15. The method of claim 14, wherein said at least one additional agent which blocks platelet aggregation is a platelet glycoprotein GP IIb-IIIa antagonist.

16. The method of claim 15, wherein said GP IIb-IIIa antagonist is eptifibatide.

17. A method for the treatment of an inflammatory disorder associated with platelet transfusion wherein a CD154 inhibitor is administered to a platelet transfusion recipient in a manner selected from the group consisting of: prior to platelet transfusion, concurrent with platelet transfusion, subsequent to platelet transfusion, as a therapeutic profile administration which includes quick onset of the effective dose of CD154 inhibitor in combination with a release formulation that permits steady release, and any combination thereof.

18. The method of claim 17, wherein the therapeutic profile of CD154 inhibitor administration includes quick onset of the effective dose in combination with a release formulation that permits steady release.

19. The method of claim 17, wherein the CD154 inhibitor is a metalloproteinase inhibitor.

20. The method of claim 19, wherein the therapeutic profile of metalloproteinase inhibitor administration includes quick onset of the effective dose in combination with a release formulation that permits steady release.

21. The method of claim 19, wherein the metalloproteinase inhibitor is $HONHCOCH_2CH(CH_2CH(CH_3)_2$—CO—NaI-Ala-NHCH$_2$CH$_2$NH$_2$(TAPI-1) or tissue inhibitor of metalloprotease-2 (TIMP-2).

22. A method of inhibiting the release of soluble CD154 from a platelet sample, comprising incubating the platelets in a container with an effective amount of a CD154 inhibitor, wherein the CD154 inhibitor is added to the container prior to or after the addition of the platelets.

23. The method of claim 22, wherein said CD154 inhibitor is a metalloproteinase inhibitor.

24. The method of claim 23, wherein the metalloproteinase inhibitor is selected from the group consisting of: $HONHCOCH_2CH(CH_2CH(CH_3)_2$—CO—NaI-Ala-NHCH$_2$CH$_2$NH$_2$(TAPI-1), tissue inhibitor of metalloprotease-2 (TIMP-2), doxycycline, galardin and SB-3CT (MMP2/MMP9 inhibitor VI).

25. The method of claim 22, wherein said incubating the platelets in a container with an effective amount of a CD154 inhibitor is during the storage of said platelets.

26. The method of claim 22, wherein the platelets are treated with an effective amount of CD154 inhibitor after storage but prior to administration to the platelet transfusion recipient.

27. The method of claim 22, wherein the platelet sample is further treated with at least one additional agent which blocks platelet aggregation or which enhances thrombolysis.

28. The method of claim 27, wherein said at least one additional agent which blocks platelet aggregation is a platelet glycoprotein GP IIb-IIIa antagonist.

29. The method of claim 28, wherein said GP IIb-IIIa antagonist is eptifibatide.

30. A container comprising a CD154 inhibitor.

31. The container of claim 30 which is a blood collection bag.

32. The container of claim 30 which is a platelet storage container.

33. The container of claim 30, wherein said CD154 inhibitor is a metalloproteinase inhibitor.

34. The container of claim 30 which is a blood collection bag.

35. The container of claim 30 which is a platelet storage container.

36. The container of claim 33, wherein said metalloproteinase inhibitor is selected from the group consisting of: $HONHCOCH_2CH(CH_2CH(CH_3)_2$—CO—NaI-Ala-NHCH$_2$CH$_2$NH$_2$(TAPI-1), tissue inhibitor of metalloprotease-2 (TIMP-2), doxycycline, galardin and SB-3CT (MMP2/MMP9 inhibitor VI).

37. The container of claim 30, wherein the container further comprises at least one additional agent which blocks platelet aggregation or which enhances thrombolysis.

38. The container of claim 37, wherein said at least one additional agent which blocks platelet aggregation is a platelet glycoprotein GP IIb-IIIa antagonist.

39. The container of claim 38, wherein said GP IIb-IIIa antagonist is eptifibatide.

40. A container comprising at least one agent which blocks platelet aggregation or which enhances thrombolysis.

41. The container of claim 40 which is a blood collection bag.

42. The container of claim 40 which is a platelet storage container.

43. The container of claim 40, wherein said at least one agent which blocks platelet aggregation is a platelet glycoprotein GP IIb-IIIa antagonist.

44. The container of claim 43, wherein said GP IIb-IIIa antagonist is eptifibatide.

* * * * *